(12) United States Patent
Isaacs

(10) Patent No.: US 10,500,630 B2
(45) Date of Patent: *Dec. 10, 2019

(54) SYSTEMS, DEVICES, AND METHODS FOR DESIGNING AND FORMING A SURGICAL IMPLANT

(71) Applicant: NuVasive, Inc., San Diego, CA (US)

(72) Inventor: Robert E. Isaacs, Chapel Hill, NC (US)

(73) Assignee: NuVasive, Inc., San Diego, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 15/496,628

(22) Filed: Apr. 25, 2017

(65) Prior Publication Data

US 2017/0224398 A1 Aug. 10, 2017

Related U.S. Application Data

(63) Continuation of application No. 14/049,183, filed on Oct. 8, 2013, now Pat. No. 9,636,181, which is a
(Continued)

(51) Int. Cl.
*A61B 17/88* (2006.01)
*B21F 45/00* (2006.01)
(Continued)

(52) U.S. Cl.
CPC ........ *B21F 45/008* (2013.01); *A61B 17/7011* (2013.01); *A61B 17/8863* (2013.01);
(Continued)

(58) Field of Classification Search
None
See application file for complete search history.

(56) References Cited

U.S. PATENT DOCUMENTS

| 3,365,804 A | 1/1968 | Fjellstrom |
| 4,282,737 A | 8/1981 | Maples |

(Continued)

FOREIGN PATENT DOCUMENTS

| CN | 202982181 U | 6/2013 |
| DE | 10314882 A1 | 10/2004 |

(Continued)

OTHER PUBLICATIONS

Langlotz et al. "A Pilot Study on Computer-Assisted Optimal Contouring of Orthopedic Fixation Devices". Computer Aided Surgery vol. 4 (1999): 305-313.

(Continued)

*Primary Examiner* — Ramesh B Patel

(57) ABSTRACT

A method is provided for determining the shape of a surgical linking device that is to be attached to a bony body structure such as the spinal column based on digitized locations of a plurality of attachment elements engaged to the bony structure. The method is implemented by a computer system through a GUI to generate an initial bend curve to mate with the plurality of attachment elements. The initial bend curve may be simplified based on user input to the GUI to reduce the number of bends necessary to produce a well-fitting linking device and may be altered to help obtain the goals of surgery.

20 Claims, 31 Drawing Sheets

Related U.S. Application Data continuation of application No. 12/417,937, filed on Apr. 3, 2009, now Pat. No. 8,549,888, which is a continuation-in-part of application No. 12/246,581, filed on Oct. 7, 2008, now Pat. No. 7,957,831, which is a continuation-in-part of application No. 12/098,375, filed on Apr. 4, 2008, now abandoned.

(51) Int. Cl.
   *G06F 17/50* (2006.01)
   *A61B 34/10* (2016.01)
   *A61B 17/70* (2006.01)
   *G16H 50/50* (2018.01)

(52) U.S. Cl.
   CPC .............. *A61B 34/10* (2016.02); *G06F 17/50* (2013.01); *A61B 2034/108* (2016.02); *G16H 50/50* (2018.01)

(56) References Cited

U.S. PATENT DOCUMENTS

| | | | |
|---|---|---|---|
| 4,474,046 A | 10/1984 | Cook | |
| 4,773,402 A | 9/1988 | Asher | |
| 5,113,685 A | 5/1992 | Asher | |
| 5,161,404 A | 11/1992 | Hayes | |
| 5,257,184 A | 10/1993 | Mushabac | |
| 5,290,289 A | 3/1994 | Sanders | |
| 5,365,996 A | 11/1994 | Crook | |
| 5,389,099 A | 2/1995 | Hartmeister | |
| 5,490,409 A | 2/1996 | Weber | |
| 5,548,985 A | 8/1996 | Yapp | |
| 5,658,286 A | 8/1997 | Sava | |
| 5,672,175 A | 9/1997 | Martin | |
| 5,682,886 A | 11/1997 | Delp | |
| 5,704,937 A | 1/1998 | Martin | |
| 5,768,134 A | 6/1998 | Swaelens | |
| 5,806,521 A | 9/1998 | Morimoto | |
| 5,819,571 A | 10/1998 | Johnson | |
| 5,819,580 A | 10/1998 | Gauthier | |
| 5,901,600 A | 5/1999 | Decker | |
| 6,006,581 A | 12/1999 | Holmes | |
| 6,035,691 A * | 3/2000 | Lin | A61B 17/8863 72/212 |
| 6,205,411 B1 | 3/2001 | Digioia, III | |
| 6,226,548 B1 | 5/2001 | Foley | |
| 6,236,875 B1 | 5/2001 | Bucholz | |
| 6,287,335 B1 * | 9/2001 | Drasler | A61F 2/07 623/1.14 |
| 6,301,495 B1 | 10/2001 | Gueziec | |
| 6,327,491 B1 | 12/2001 | Franklin | |
| 6,330,964 B1 * | 12/2001 | Kayan | A61B 17/0684 227/176.1 |
| 6,332,780 B1 | 12/2001 | Traxel | |
| 6,347,240 B1 | 2/2002 | Foley | |
| 6,529,765 B1 | 3/2003 | Franck | |
| 6,578,280 B2 | 6/2003 | Kinoshita | |
| 6,644,087 B1 | 11/2003 | Ralph | |
| 6,701,174 B1 * | 3/2004 | Krause | A61B 17/025 378/21 |
| 6,906,724 B2 | 6/2005 | Lake | |
| 6,978,188 B1 | 12/2005 | Christensen | |
| 7,206,626 B2 * | 4/2007 | Quaid, III | A61B 17/3403 600/407 |
| 7,454,939 B2 | 11/2008 | Garner | |
| 7,837,467 B2 | 11/2010 | Butscher | |
| 7,957,831 B2 * | 6/2011 | Isaacs | A61B 17/7011 700/165 |
| 8,549,888 B2 * | 10/2013 | Isaacs | A61B 17/7011 72/31.04 |
| 9,636,181 B2 * | 5/2017 | Isaacs | A61B 17/7011 |
| 2002/0007294 A1 | 1/2002 | Bradbury | |
| 2002/0133097 A1 | 9/2002 | Leitner | |
| 2002/0183610 A1 | 12/2002 | Foley | |
| 2003/0055435 A1 | 3/2003 | Barrick | |
| 2003/0055502 A1 | 3/2003 | Lang | |
| 2003/0149351 A1 | 8/2003 | Nowinski | |
| 2003/0205075 A1 | 11/2003 | Strippgen | |
| 2003/0215122 A1 | 11/2003 | Tanaka | |
| 2004/0068187 A1 * | 4/2004 | Krause | A61B 17/15 600/443 |
| 2004/0097952 A1 | 5/2004 | Sarin | |
| 2004/0122549 A1 * | 6/2004 | Otsuki | G05B 19/4103 700/189 |
| 2004/0133276 A1 | 7/2004 | Lang | |
| 2004/0147927 A1 | 7/2004 | Tsougarakis | |
| 2004/0152972 A1 | 8/2004 | Hunter | |
| 2004/0158260 A1 | 8/2004 | Blau | |
| 2004/0167637 A1 | 8/2004 | Biscup | |
| 2005/0054917 A1 | 3/2005 | Kitson | |
| 2005/0101966 A1 | 5/2005 | Lavallee | |
| 2005/0119593 A1 | 6/2005 | Gallard | |
| 2005/0149050 A1 | 7/2005 | Stifter | |
| 2005/0182320 A1 | 8/2005 | Stifter | |
| 2005/0192575 A1 | 9/2005 | Pacheco | |
| 2005/0203511 A1 | 9/2005 | Wilson-MacDonald | |
| 2005/0245817 A1 | 11/2005 | Clayton | |
| 2005/0251139 A1 | 11/2005 | Roh | |
| 2005/0262911 A1 * | 12/2005 | Dankowicz | B21D 7/14 72/31.04 |
| 2005/0288809 A1 | 12/2005 | Spaeth | |
| 2006/0005601 A1 | 1/2006 | Widmayer | |
| 2006/0015030 A1 | 1/2006 | Poulin | |
| 2006/0094951 A1 | 5/2006 | Dean | |
| 2006/0120583 A1 | 6/2006 | Dewaele | |
| 2006/0150699 A1 * | 7/2006 | Garner | A61B 17/8863 72/31.04 |
| 2006/0212158 A1 | 9/2006 | Miller | |
| 2006/0235338 A1 | 10/2006 | Pacheco | |
| 2006/0247864 A1 | 11/2006 | Tamez-Pena | |
| 2006/0264934 A1 | 11/2006 | Fallin | |
| 2006/0264973 A1 | 11/2006 | Abdelgany | |
| 2006/0282020 A1 | 12/2006 | Bertagnoli | |
| 2007/0066917 A1 | 3/2007 | Hodorek | |
| 2007/0093824 A1 | 4/2007 | Hestad | |
| 2007/0093998 A1 | 4/2007 | El-Baroudi | |
| 2007/0118055 A1 | 5/2007 | McCombs | |
| 2007/0118243 A1 | 5/2007 | Schroeder | |
| 2007/0142751 A1 * | 6/2007 | Kang | G06F 19/00 600/587 |
| 2007/0198022 A1 | 8/2007 | Lang | |
| 2007/0227216 A1 | 10/2007 | Schalliol | |
| 2007/0233246 A1 | 10/2007 | Trieu | |
| 2007/0239159 A1 | 10/2007 | Altarac | |
| 2007/0250169 A1 | 10/2007 | Lang | |
| 2007/0276501 A1 | 11/2007 | Betz | |
| 2008/0009945 A1 | 1/2008 | Pacheco | |
| 2008/0039717 A1 | 2/2008 | Frigg | |
| 2008/0065067 A1 | 3/2008 | Steinberg | |
| 2008/0154120 A1 | 6/2008 | Von Jako | |
| 2008/0167547 A1 | 7/2008 | Bova | |
| 2008/0208080 A1 | 8/2008 | Ichikawa | |
| 2008/0269596 A1 | 10/2008 | Revie | |
| 2008/0269898 A1 | 10/2008 | Carls | |
| 2008/0269906 A1 | 10/2008 | Iannotti | |
| 2008/0288229 A1 | 11/2008 | Arvizo | |
| 2008/0306490 A1 | 12/2008 | Lakin | |
| 2009/0022382 A1 | 1/2009 | Feikas | |
| 2009/0024164 A1 | 1/2009 | Neubardt | |
| 2009/0043556 A1 | 2/2009 | Axelson | |
| 2009/0082666 A1 | 3/2009 | Geist | |
| 2009/0089034 A1 | 4/2009 | Penney | |
| 2009/0093852 A1 | 4/2009 | Hynes | |
| 2009/0099605 A1 | 4/2009 | Fallin | |
| 2009/0132050 A1 | 5/2009 | Holm | |
| 2009/0149977 A1 | 6/2009 | Schendel | |
| 2009/0157083 A1 | 6/2009 | Park | |
| 2009/0157185 A1 | 6/2009 | Kim | |
| 2009/0209851 A1 | 8/2009 | Blau | |
| 2009/0209884 A1 | 8/2009 | Van Vorhis | |
| 2009/0226055 A1 | 9/2009 | Dankowicz | |
| 2009/0226068 A1 | 9/2009 | Fitz | |

(56) References Cited

U.S. PATENT DOCUMENTS

| | | |
|---|---|---|
| 2009/0254097 A1* | 10/2009 | Isaacs ............... A61B 17/7011 606/130 |
| 2009/0254326 A1* | 10/2009 | Isaacs ............... A61B 17/7011 703/11 |
| 2009/0276045 A1 | 11/2009 | Lang |
| 2010/0030231 A1 | 2/2010 | Revie |
| 2010/0030232 A1 | 2/2010 | Zehavi |
| 2010/0076563 A1 | 3/2010 | Otto |
| 2010/0100011 A1 | 4/2010 | Roche |
| 2010/0101295 A1 | 4/2010 | Miller |
| 2010/0111631 A1 | 5/2010 | Trieu |
| 2010/0145663 A1 | 6/2010 | Skalli |
| 2010/0177946 A1 | 7/2010 | De Bruijne |
| 2010/0191071 A1 | 7/2010 | Anderson |
| 2010/0191088 A1 | 7/2010 | Anderson |
| 2010/0191100 A1 | 7/2010 | Anderson |
| 2010/0234725 A1 | 9/2010 | Geist |
| 2010/0292795 A1 | 11/2010 | Jensen |
| 2010/0292963 A1 | 11/2010 | Schroeder |
| 2010/0329530 A1 | 12/2010 | Lang |
| 2010/0332197 A1 | 12/2010 | Melton |
| 2010/0332248 A1 | 12/2010 | Pettersson |
| 2011/0010187 A1 | 1/2011 | Andersson |
| 2011/0015514 A1 | 1/2011 | Skalli |
| 2011/0040340 A1 | 2/2011 | Miller |
| 2011/0066193 A1 | 3/2011 | Lang |
| 2011/0071802 A1 | 3/2011 | Bojarski |
| 2011/0093023 A1 | 4/2011 | Lee |
| 2011/0093108 A1 | 4/2011 | Ashby |
| 2011/0094278 A1 | 4/2011 | Caporusso |
| 2011/0107270 A1 | 5/2011 | Wang |
| 2011/0144752 A1 | 6/2011 | Defelice |
| 2011/0196426 A1 | 8/2011 | Peukert |
| 2011/0245871 A1 | 10/2011 | Williams |
| 2011/0257653 A1 | 10/2011 | Hughes |
| 2011/0265538 A1 | 11/2011 | Trieu |
| 2011/0266265 A1 | 11/2011 | Lang |
| 2011/0268325 A1 | 11/2011 | Teichman |
| 2011/0270262 A1 | 11/2011 | Justis |
| 2011/0295378 A1 | 12/2011 | Bojarski |
| 2011/0305379 A1 | 12/2011 | Mahfouz |
| 2011/0307020 A1 | 12/2011 | Geist |
| 2011/0319745 A1 | 12/2011 | Frey |
| 2012/0010710 A1 | 1/2012 | Frigg |
| 2012/0016423 A1 | 1/2012 | Hua |
| 2012/0047980 A1 | 3/2012 | Harper |
| 2012/0063655 A1 | 3/2012 | Dean |
| 2012/0116203 A1 | 5/2012 | Vancraen |
| 2012/0141034 A1 | 6/2012 | Iannotti |
| 2012/0178069 A1 | 7/2012 | McKenzie |
| 2012/0186411 A1 | 7/2012 | Lodahi |
| 2012/0191192 A1 | 7/2012 | Park |
| 2012/0209394 A1 | 8/2012 | Bojarski |
| 2012/0230566 A1 | 9/2012 | Dean |
| 2012/0247173 A1 | 10/2012 | Paris |
| 2012/0274631 A1 | 11/2012 | Friedland |
| 2012/0290272 A1 | 11/2012 | Bryan |
| 2012/0310364 A1 | 12/2012 | Li |
| 2012/0323279 A1 | 12/2012 | Tsuang |
| 2012/0325363 A1 | 12/2012 | Knebl |
| 2013/0053854 A1 | 2/2013 | Schoenefeld |
| 2013/0072982 A1 | 3/2013 | Simonson |
| 2013/0073315 A1 | 3/2013 | Cardamone |
| 2013/0090692 A1 | 4/2013 | Nuckley |
| 2013/0091921 A1 | 4/2013 | Wilcox |
| 2013/0110174 A1 | 5/2013 | Marik |
| 2013/0123850 A1 | 5/2013 | Schoenefeld |
| 2013/0131486 A1 | 5/2013 | Copf |
| 2013/0166256 A1 | 6/2013 | Wirx-Speetjens |
| 2013/0211531 A1 | 8/2013 | Steines |
| 2013/0218163 A1 | 8/2013 | Frey |
| 2013/0238096 A1 | 9/2013 | Kotlus |
| 2013/0245803 A1 | 9/2013 | Lang |
| 2013/0268007 A1 | 10/2013 | Rezach |
| 2013/0296954 A1 | 11/2013 | Skaggs |
| 2013/0304217 A1 | 11/2013 | Recber |
| 2013/0307955 A1 | 11/2013 | Deitz |
| 2013/0325069 A1 | 12/2013 | Pereiro De Lamo |
| 2013/0332128 A1 | 12/2013 | Miles |
| 2013/0345757 A1 | 12/2013 | Stad |
| 2014/0025181 A1 | 1/2014 | Vanasse |
| 2014/0066994 A1 | 3/2014 | Dominik |
| 2014/0074438 A1 | 3/2014 | Furrer |
| 2014/0076883 A1 | 3/2014 | Brailovski |
| 2014/0081400 A1 | 3/2014 | Azernikov |
| 2014/0137618 A1 | 5/2014 | Isaacs |
| 2014/0213889 A1 | 7/2014 | Macht |
| 2014/0244220 A1 | 8/2014 | McKinnon |
| 2014/0257508 A1 | 9/2014 | Bojarski |
| 2014/0311203 A1 | 10/2014 | Crawford |
| 2014/0364916 A1 | 12/2014 | Lorio |

FOREIGN PATENT DOCUMENTS

| | | |
|---|---|---|
| DE | 102004008870 A1 | 10/2004 |
| EP | 1413257 A1 | 10/2002 |
| EP | 1426023 A1 | 10/2003 |
| EP | 1657681 A1 | 5/2006 |
| EP | 2017785 A1 | 1/2009 |
| EP | 2522295 A1 | 11/2012 |
| JP | 2013230221 A | 11/2013 |
| WO | WO-2003030787 A1 | 4/2003 |
| WO | WO-2004070581 A2 | 8/2004 |
| WO | WO-2006055998 A1 | 6/2006 |
| WO | WO-2007009263 A1 | 1/2007 |
| WO | WO-2008021494 A2 | 2/2008 |
| WO | WO-2008101090 A2 | 8/2008 |
| WO | WO-2008130355 A1 | 10/2008 |
| WO | WO-2009035358 A1 | 3/2009 |
| WO | WO-2009140294 A1 | 11/2009 |
| WO | WO-2010099231 A2 | 9/2010 |
| WO | WO-2012061452 A1 | 5/2012 |
| WO | WO-2012062464 A1 | 5/2012 |
| WO | WO-2012135653 A1 | 10/2012 |
| WO | WO-2012152900 A1 | 11/2012 |
| WO | WO-2013087082 A1 | 6/2013 |
| WO | WO-2013134623 A1 | 9/2013 |
| WO | WO-2013150233 A1 | 10/2013 |
| WO | WO-2014016824 A1 | 1/2014 |
| WO | WO-2013041618 A1 | 3/2014 |
| WO | WO-2014037093 A1 | 3/2014 |
| WO | WO-2014048448 A1 | 4/2014 |
| WO | WO-2014070889 A1 | 5/2014 |
| WO | WO-2014079812 A1 | 5/2014 |
| WO | WO-2014088801 A1 | 6/2014 |
| WO | WO-2014107144 A1 | 7/2014 |

OTHER PUBLICATIONS

International Search Report for related International Application No. PCT/US2009/039452, dated Jul. 14, 2009, 3 pages.

Written Opinion of the International Searching Authority for related International Application No. PCT/US2009/039452, dated Jul. 14, 2009, 7 pages.

* cited by examiner

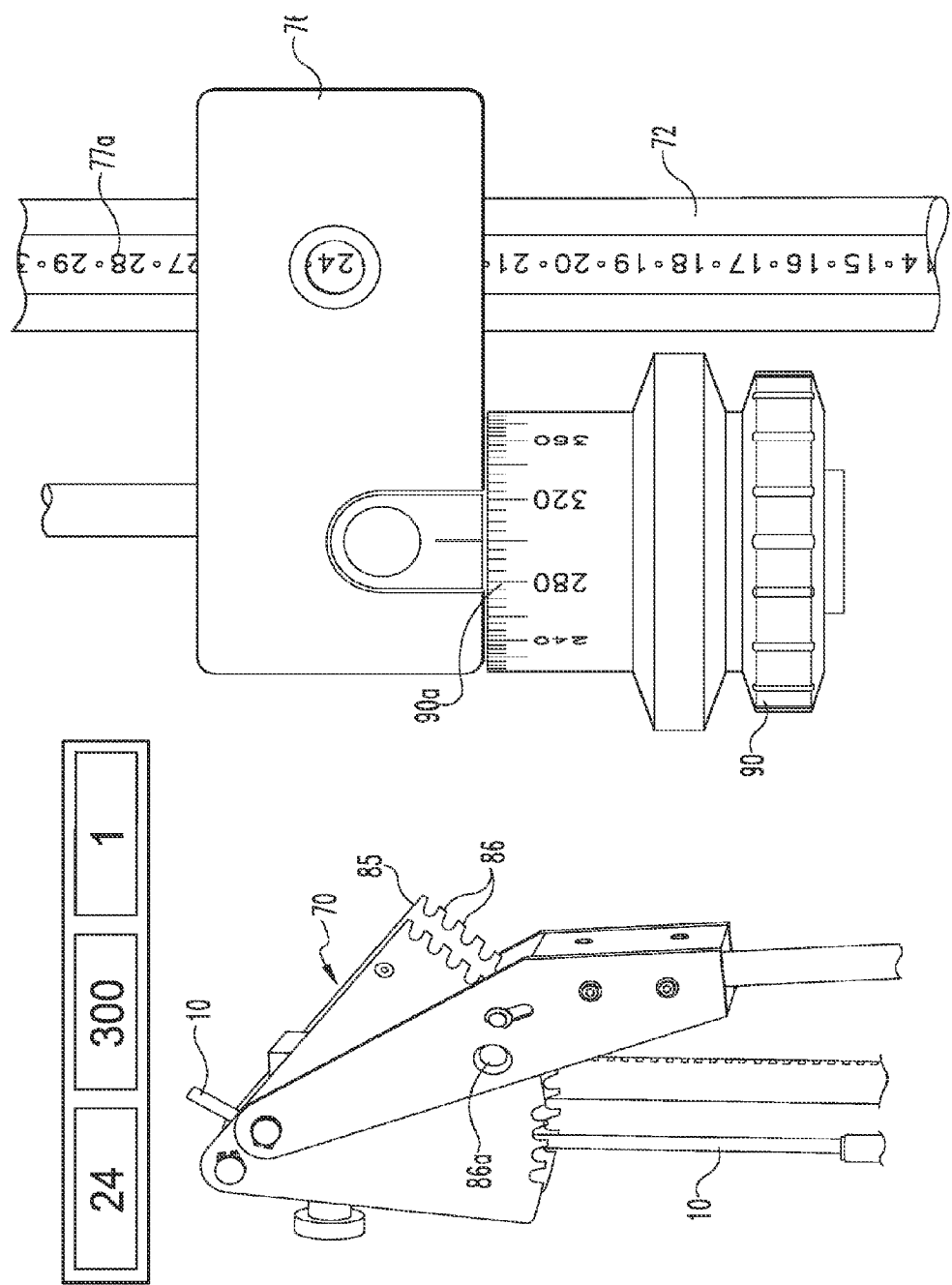

Fig. 18b (Cont.)

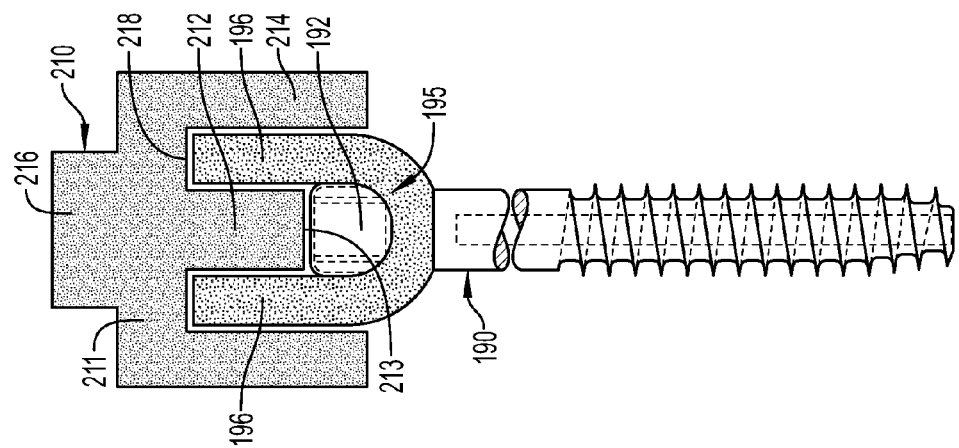
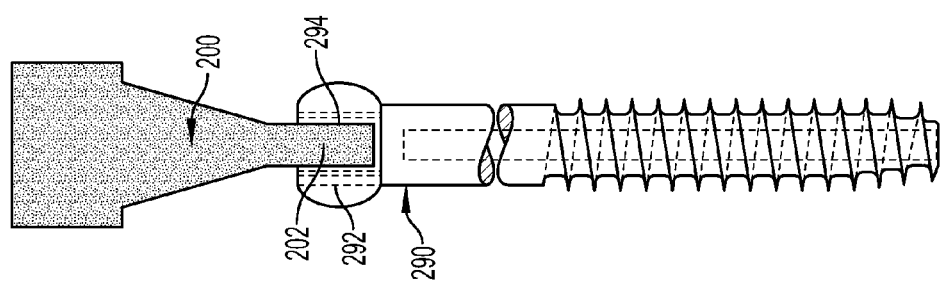
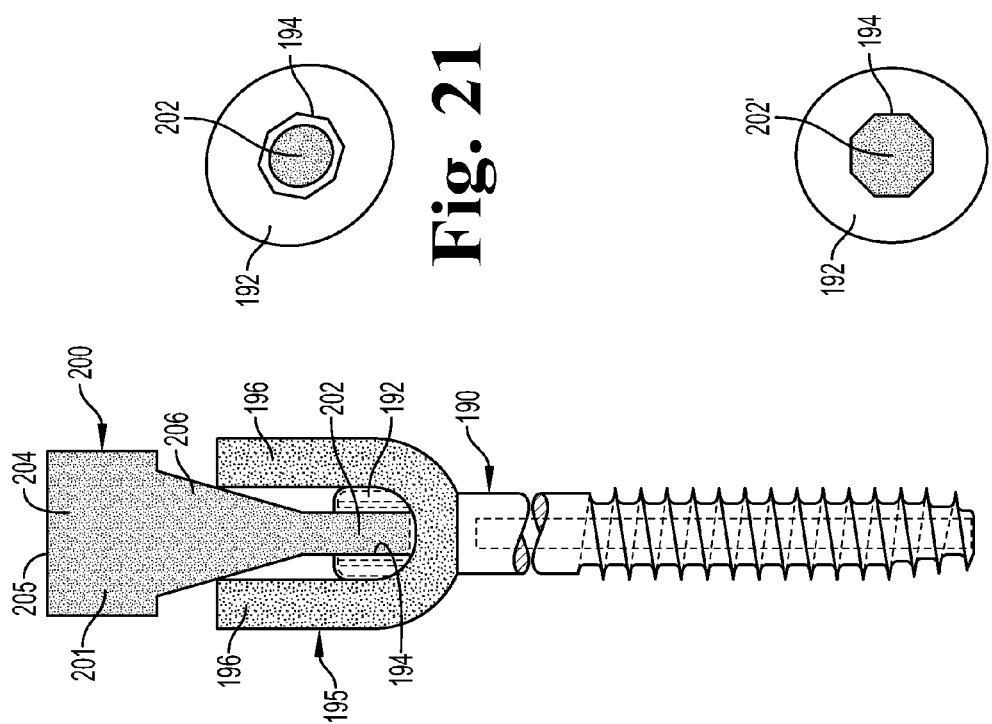

SYSTEMS, DEVICES, AND METHODS FOR DESIGNING AND FORMING A SURGICAL IMPLANT

CROSS-REFERENCE TO RELATED APPLICATIONS

This application is a continuation of U.S. application Ser. No. 14/049,183 (now U.S. Pat. No. 9,636,181), filed on Oct. 8, 2013, which is a continuation of U.S. application Ser. No. 12/417,937 (now U.S. Pat. No. 8,549,888), filed on Apr. 3, 2009, which is a continuation in part of U.S. application Ser. No. 12/246,581 (U.S. Pat. No. 7,957,831), filed on Oct. 7, 2008, which is a continuation in part of U.S. application Ser. No. 12/098,375, filed on Apr. 4, 2008 the entire contents of which are incorporated by reference as if set forth in their entirety herein.

BACKGROUND

The present invention is directed systems, devices, and methods related to the design and formation of surgical implants such as surgical linking devices. More particularly the present invention provides systems, devices, and methods for forming or shaping a surgical implant to conform to two or more selected attachment points (including surface anatomy) in a six degree of freedom method for attachment.

Fixation systems for aligning, adjusting and or fixing, either partially or rigidly, portions of a patient's bony anatomy in a desired spatial relationship relative to each other are frequently used in orthopedic surgery. For example, in spinal surgery for repair or positional adjustment of the vertebrae, it is often necessary that multiple vertebrae are surgically manipulated. As spinal surgery often requires the instrumentation of more bony elements than other areas of orthopedic surgery, the linkage devices can be extremely challenging to design and implant. Treatment for conditions such as scoliosis, spinal injury, disk problems and the like often make use of spinal rod fixation systems for positioning the vertebrae and supporting the spinal motion segments.

A spinal rod needs to be oriented in six degrees of freedom to compensate for the anatomical structure of the particular patient's spine and the particular attachment points or methods for attaching the rods to the vertebrae. In addition, the physiological problem being treated as well as physician's preferences will determine the exact configuration necessary. Accordingly, the size, length and particular bends of each spinal rod depends on the size, number and position of each vertebra to be constrained, their spatial relationship as well as the fixating means, such as pedicle screws, used to hold the rods attached to each vertebra. The relationship of the vertebrae will be different for each patient and the positioning of the patient at the point of installation of the rods. During surgery, the orientation of the spine and vertebrae can be very different than the corresponding position of a patient's upright posture. Rods are bent in one or more anatomic planes measured by distance from each bend, angle of the bend and rotation in relationship to other bend points in order to fit into two or more vertebral anchors.

The bending of a spinal rod can be accomplished by a number of methods. The oldest and most widely used method for bending rods manually during surgery is a three-point bender called a French Bender in which a bending pliers type device is manually operated to place one or more bends in a rod. The French Bender requires both hands to operate and provides leverage based on the length of the handle. While the device can make it relatively easy to bend a spinal rod, the determination of the location, angle and rotation of bends using such a device is often arbitrary. Problems can thus occur from bending a device and then rebending to fix mistakes which impose metal fatigue or stress risers into a rod thus increasing the risk of a mechanical failure. Increased time in the operating room (OR) to achieve optimum bending of the rod can increase the chance of morbidity.

Spinal rods are usually formed of stainless steel, titanium or other similarly hard metal, and as such are difficult to bend without some sort of leverage-based bender. In addition, since several spatial relationships have to be maintained in using a French Bender, the process can take an extremely long time and its use requires a great degree of physician skill to accomplish an accurate final product. Even still it is difficult to achieve a well-shaped rod using the French Bender. Accordingly, various ways have been attempted to overcome the limitations of the current technology.

A number of manual benders are described in the art. In U.S. Pat. No. 5,113,685 issued May 19, 1992 to Asher et al, there is described an apparatus for use in bending rods and plates to the spinal column comprising an elongated bar with a variety of bending angles for bending more angles than the French Bender. However, this device is hard to use and provides no means for determining the six degrees of spatial relationship that each bend must make. In US patent application 2006/0150699 published Jul. 13, 2006 to Garner, et al, there is an instrument and method for bending rod using a lever pliers type device having bearing surfaces. In addition, the angle of bend can be determined by use of a gauge that indicates angle bend by degree of grip movement. While this device may be easier to use, it does not aid in determination of the other degrees of freedom either in calculating them or in making the final bends.

An automatic method designed for pre-surgical formation of spinal rods is disclosed in US patent application 2005/0262911 published Dec. 1, 2005 to Dankowicz, et al. An automatic series of shaping steps is "imposed" on a rod from an input mechanism for producing the desired multi-dimensional bent shape. One problem with this device is that it relies on a pre-surgical determination of the points at which bends occur to determine the final shape of the rod. While it is possible to anticipate where the anchors might ideally end up and occasionally be correct, surgical implantation of attachment points is as much art as science so a preformed rod may not be accurately produced when compared to the anchor means as they are actually installed in the spine. This can lead to a highly problematic circumstance in which the surgical site has been opened and the surgeon has a rod that does not fit the attachment points. Further disadvantages are that the device is large and that some surgeons still would prefer a manual means of producing a rod during surgery because of the ability to make minute adjustments based on feedback during surgery.

Effort has been directed to computer-aided design or shaping of spinal rods, but these efforts have been largely unsuccessful due to the lack of bending devices as well as a lack of understanding of all the issues involved in bending surgical devices. For example, an article entitled "A pilot study on computer-assisted optimal contouring of orthopedic fixation devices," Computer Aided Surgery, 1999; 4 (6):305-13, indicated that overcoming these problems would be difficult if not impossible.

Image guided surgical systems, for example, devices produced by BrainLAB, as well as three dimensional digitizers are already in the art and some are already FDA approved for use during surgery. These devices are fairly commonly used by some physicians in the operating environment. By moving the digitizer through space or inputting a particular point in space, a map can be produced of spatial relationships. In U.S. Pat. No. 6,400,131, issued on Dec. 31, 2002 to Leitner et al., there is described a contour mapping system applicable as a spine analyzer and probe. The device is disclosed as being used to determine the curvature of the spine while standing and contour mapping of the spine in the intact (non-surgical) patient.

Accordingly, a means for designing and forming a surgical linking device, especially for linking bony parts of the body, for use in a surgical orthopedic procedure such as the attachment of a spinal rod, that is accurate, quick and takes the various input characteristics into account for the specific implanted device as actually needed would be of great value during an orthopedic implant surgery such as spinal surgery.

SUMMARY

In one embodiment there is a system for shaping a surgical linking device for attachment to a selected bony body structure having at least two linking device attachment elements comprising:
  a) a means for determining the relative spatial location of at least one of the attachment means and the bony structure;
  b) a means for converting the relative spatial location into a digital format;
  c) a computer capable of receiving this digital format and using the relative spatial location to determine one or more shape locations in the surgical linking device, each shape location having one or more of a shape angle and shape rotation at each one or more shape locations such that shaping of the surgical linking device will enable the surgical linking device to attach to the bony body structure using the attachment elements; and
  d) a means for delivering the determined shape information to a computer output.

In yet another embodiment there is a surgical linking device on a selected bony body structure comprising:
  a) placing at least two linking device attachment elements on the bony body structure at desired locations;
  b) digitally determining the relative spatial location of at least one of the bony structure and the attachment elements;
  c) transferring the digitized information to a computer which determines information of one or more of:
    i) one or more of the location, angle and rotation of shapes in a selected surgical linking device that could be made in order for the linking device to be attached to the bony structure using the attachment elements;
    ii) one or more adjustments to the position of or addition to the attachment elements that could be made so that a selected preformed, partially preformed or a minimally shaped surgical linking device can be attached to the bony structure with the attachment elements;
    iii) one or more mathematical adjustments to the digitally rendered position of the attachment elements so that the final shaped surgical linking device, once attached to the bony structure, will correct or alter the shape of the bony structure(s);
  d) delivering the computer determined information to a computer output;
  e) using the information from the computer output to perform one or more of:
    i) selecting a preformed or partially preformed surgical linking device;
    ii) shaping a surgical linking device with a device that measures one or more of the shape location, shape angle and shape rotation; and
    iii) adjusting the position of or adding to the attachment elements; and
  f) attaching the surgical linking device to the attachment elements.

Yet another embodiment includes a device for bending a surgical linking device, in which the device is particularly suited for manual operation, comprising:
  a) a lever for bending the linking device; and
  b) at least two bend measuring means selected from the group comprising: bend position measuring means, bend angle measuring means and bend rotation measuring means.

Another embodiment of the invention includes a device for determining the rotation for placing a bend in a surgical linking device comprising:
  a) a circular gauge indicating the degrees of rotation; and
  b) a means for positioning the device on the surgical linking device or on a means for bending the linking device such that the gauge aligns with any bends in the linking device.

Yet still another embodiment is a means for determining the selection of a preformed surgical linking device for use in attaching to a selected bony body structure having at least two linking device attachment elements comprising:
  a) a means for determining the relative spatial location of each attachment elements;
  b) a means for converting the relative spatial location into a digital format;
  c) a plurality of preformed surgical linking devices;
  d) a computer having selected spatial information about the preformed linking devices wherein the computer is capable of receiving the digital format in b) and using the digital format to determine if one of the preformed surgical linking devices fits the attachment elements and if there is none that fit, if one or more attachment elements could be adjusted in relative location such that one of the preformed surgical linking devices could be selected and fit the attachment elements; and
  e) a means for delivering the determined attachment elements adjustments and selected preformed linking device to a computer output.

A further embodiment contemplates a method for placing multiple bends with 6 degrees of freedom in a surgical linking device comprising:
  a) establishing a starting point on the device;
  b) holding the device relative to the starting point;
  c) moving the device and measuring away from the starting point to establish a second point on the device for placing a bend with 6 degrees of freedom; and
  d) repeating steps b) and c) using either the starting point or the second point to hold from until the multiple bends are completed.

Another embodiment of the present invention is a process for producing one or more shapes in a surgical linking device comprising:
  a) a digital process for determining the desired spatial parameters of the shapes to be produced; and b) a shaping process linked to the digital process wherein the shaping process applies the spatial parameters to the surgical attachment device, in which the shaping process is particularly suited for manual implementation in the surgical operating room.

In yet another embodiment, a method is provided for shaping a surgical linking device for engagement to a plurality of attachment elements engaged within the selected bony body structure, each of the attachment elements having an engagement portion for engagement with the shaped linking device, in which the method comprises:

(a) providing digitized data for the location of the plurality of attachment elements;

(b) determining a tolerance range corresponding to an acceptable distance that the shaped linking device is from the engagement portion of each attachment elements;

(c) developing a curve function to approximate the location of each of the plurality of attachment elements;

(d) calculating the location of the linking device shaped according to the curve function at the location of each of the plurality of attachment elements;

(e) calculating an error based on the difference in the calculated location of the linking device and the location of each of the plurality of attachment elements;

(f) determining if the error exceeds the tolerance range and if so determining a higher order curve function;

(g) when the error falls within the tolerance range, generating a bend curve having a discrete plurality of bend points using the curve function, the discrete plurality of bend points being distributed at a predetermined distance;

(i) generating a revised bend curve with the remaining bend points; and (j) generating bending instructions to be performed on the linking device by a bending tool at each of the remaining bend points.

In another aspect of the invention, a digitizer probe is provided that is configured to temporarily mate with the head of an implant. The probe includes a shaft accessible beyond the implant that can be used to fix the location of the implant when determining the bending protocol for a rod, plate, or elongate member to engage the implant.

BRIEF DESCRIPTION OF THE DRAWINGS

FIGS. 18a-d show a particular bend instruction as implemented using the bending tool shown in FIG. 7.

FIG. 20 is a side view of a poly-axial implant with a digitizer probe according to one embodiment of the invention engaged hereto.

FIG. 21 is a top view of the interface of the digitizer probe with the head of the implant shown in FIG. 20.

FIG. 22 is a top view of an alternative interface of the digitizer probe with the head of the implant shown in FIG. 20.

FIG. 23 is a side view of the interface of the digitizer probe with an alternative implant.

FIG. 24 is a side view of a digitizer probe according to another embodiment engaged to an implant.

DETAILED DESCRIPTION

Figure 1A:
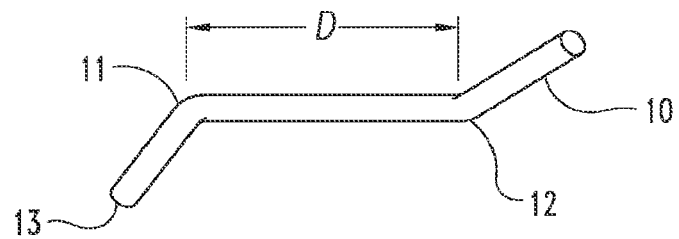
FIGS. 1a through 1d depict a surgical rod and various bends with 6 degrees of freedom.

The present invention refers to a method for improving the shaping of a surgical linking device, for example, by bending. First, by digitally calculating appropriate shapes such as bends in 6 degrees of freedom (three dimensional) and then outputting that information to the surgeon or other medical personnel or to a bending device, a linking device can be easily and quickly shaped by casting, bending or the like. Second, a device is disclosed for quickly and easily taking the input from a digitally calculated means, or other similar means, and manually shaping a precisely bent or shaped linking device. Accordingly, the time spent in surgery bending linking devices can be greatly reduced thus improving the chances of a successful operation without complications as well as reduce the cost of such an operation, for example, from rebending or bending a second device. Since a significant portion of time is spent in bending and in some cases rebending such devices, taking minutes to an hour or more off the time to bend a linking device correctly is an important advance in the art.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

It is understood that the term "coupled", as used herein, is defined as connected, although not necessarily directly, and not necessarily mechanically. The term "bending" refers to the act of forcing, or the like, a linking device from a first position at a particular point to a second angular or curved position at that point in three dimensional space. Six degrees of freedom are considered in bending a particular device once the location of the bend is determined. In general, once the position of the placement of a bend is determined, then the angle of the bend and in many cases the rotation about a central axis may also be determined. In many cases a simple angular shaping is sufficient while in others, such as is often the case for surgical rods, a rotation off axis is necessary.

The bending is exemplified in the drawings which explanation follows. As used herein "shaping" refers to not only bending but other methods of taking the 6 degrees of freedom information generated with the present invention and producing a shaped device. In addition to bending, the use of extrusion, casting, deformation, molding and the like could be considered a means of shaping a particular device with the information generated herein. See U.S. Pat. No. 6,749,614 issued Jun. 15, 2004 to Teitelbaum, et al., for an example of such material which could be used to shape a linking device with the present invention methods.

A "surgical linking device" as used herein refers to those devices used during surgery to use to bind to a selected bony body structure to mend, stabilize, move, reshape, correct deformities or strengthen such as attachments made to bones. For example, surgical rods, surgical plates, surgical transverse connecting rods, surgical wire or surgical cable and the like are used in surgery to mend, stabilize or correct breaks, correct deformities and the like in selected bones by attachment to two or more attachment points. Such plates and rods usually are supplied straight in a number of lengths or preformed arcs and must be bent to fit their intended use. (See v2-Evren 2008 online catalog, www.v2evren.com.tr for examples of vertebral rods and connectors as well as other orthopedic devices of a surgical nature). Typically, these devices are made of titanium or other extremely durable, stiff and difficult to bend material. Rigid materials such as titanium, commercially pure titanium, stainless steel, cobalt chrome and the like could be used. Other materials include flexible materials such as made of PEEK or other appropriate plastics, graphite or the like, bumpered systems and devices in both mono and multi diameter versions. Where casting or other shaping means are used, any rigid material suitable for surgical use in these conditions can be used.

Additionally, useful are shape memory alloys, shape altering devices, materials with varying stiffness, biological materials and any synthetic material with bioactive properties. In particular, the benefits of shape memory materials could be magnified by the processes described herein, especially when such processes are applied more than once on the same linking device. The shape memory materials allow an initial shape based on the location of the fixation points or facilitate rod implantation and final shape determination from the altered position. The linking device can then be used to alter the orientation of the bony structure(s) to help achieve the results of surgery. Other surgical linking devices could include plates attached to specific body parts, both in the apendicular and axial skeleton, as well as cables and rigid clamps used to affix to and alter teeth and their alignment.

The French Bender is the surgical instrument of choice today to bend these materials but it does so without regard to being able to measure the 6 degrees of freedom of movement in any manner. Accordingly, the process of bending a surgical rod with a French Bender is laborious and demanding, requires some degree of artistry and frequently requires starting over.

A "linking device attachment elements" refers to a means attached to a body structure designed to received the surgical linking device and hold it in place. Surgical clamps and screws are common examples of these devices. In the case of a surgical rod, a variety of surgical screws, bolts, and hooks are available to screw into the bone and or to hold the rods in place. These include polyaxial screws, mono axial screws, fixed angle screws, iliac screws, sacral screws, lateral mass screws, bolts, laminar hooks and pedicle hooks. In additions, items such as staples, or plates that serve to hold one body part, can serve as an anchor to which a linking device can be affixed onto the spine especially with anterior plating systems. All these systems can be used together and further connect up to similar anchoring plates.

Connectors such as axial, lateral and transverse connectors are used while locking screws are often used to hold the linking device in place. Even further, the attachment elements could be devices added to the means to change the attachment position. A screw attachment or "offset", for example, could be used. In the practice of this Invention, the devices and methods of this invention anticipate use when there are at least two and frequently three or more attachment elements corresponding to each surgical linking device. Multiple differing types of attachment elements could be used in a single installation. In addition, in the case of plates, the attachment elements may be installed after the shaping of the plate based on the shape of the plate rather than the other way around.

"Determining the relative location of each attachment elements and bony structure" refers to understanding the spatial relationship between the bony structure and any points of attachment so that a linking device such as a surgical rod can connect between the attachment points given the proper shape of the device. The relative location can be obtained with currently available image guidance devices such as three dimensional digitizers (such as the Polhemus Patriot) which can be used simply by engaging the device at several attachment points or along the bony structure and letting a computer in the device or elsewhere digitize the information. A partially manual method could be done, for example, by photographic means such as x-ray or regular photography and the spatial relationship determined away from the patient. Such a method might need a plurality of photographs but given this explanation is well within the skill in the art.

From the determination of the relative spatial location, the information can easily be digitized either automatically, as is the case with the three dimensional digitizer, or by entering hand calculated information into a computer or the like which then stores the information digitally. Either way, the information is converted into a digital format which a computer is capable of manipulating. Other devices could be optical, EM, image guidance systems, Shape Tape™, ultrasound, cat scans, and other radiographic devices. The key is that information needs to be gathered about spatial relationships and that information is capable of being obtained in a variety of ways. It is clear that the enumerated means or any other means which achieves the determination of the spatial relationship can be used by one skilled in the art. In some embodiments the expression "determining the relative location of each attachment means and bony structure" may also refer to making multiple determinations after adjustments to the installation or attachments means are made. One skilled in the art will know when and how to make such multiple determinations.

Since structures such as the shape of the patient's anatomy, bone structure, other devices in the area and the like may also need to be considered when determining the bend profile, the invention further contemplates that other structural information may also be created in a digital format for transfer or use by a computer. In one embodiment, the contour or structure can serve as the input by itself, such as with any plating system, where the input is the topography of the surface of the body part, with this input being used to guide shaping the implant. The attachment points are then driven through the plate after the plate is shaped, not prior, in as much as the information could be determined solely from surface anatomy and not the attachment points.

A computer such as a laptop, hand held device, desktop or other computer device can receive the relative location of the attachment elements and/or the bony structure in a digital format. The computer then programmed with the spatial information can determine the best way to shape, bend or the like, the linking device in order to fit the attachment elements. This determination of bends also takes into consideration the fact that other structures or the shape of the structure being attached to may be in the way. For example, in a spinal procedure, the shape of the vertebrae bones must also be considered.

The computer can be programmed to accommodate any number of parameters in determining the output or the final shape of the linking device. In this way, the goals of surgery can be assisted through the alteration of the shape of the linking device. Whereas in one embodiment, the shape dictated by the information above and not altered further could be used to create the linking device, further alterations in the device's shape can help to address, straighten, or alter abnormalities in alignment of the body part(s), create lessen or eliminate deformities, reduce or impose changes in alignment or the addition or elimination of stresses. It is possible to couple the changes in different planes or simply apply correction in one plane, rather than in another orthogonal plane. These modifications of the shaping information that is outputted can be obtained through various means-visual, anatomic, guided by radiographs (intraoperative, preoperative, positioning films, etc.), guided by the material properties of the linking device and the plasticity and/or relative location of the body part(s) being altered.

The computer need not have direct interaction with the device used for bending, in one embodiment. In other embodiments, it could input the information directly to the shaping device such as to a screen or other means such as to set the dials prior to shaping. The computer defines mathematically from the spatial location of the attachment means and the bony structure of the body, the heads of screws, surface of that bony body part and the like, a curve which approaches these points in three dimensional space within the requirements and capabilities of the selected surgical linking device. The determined information can be used to select a specific device, to place bends in an unbent or pre-bent device (or shape as needed) or to adjust the attachment means as desired. In addition, a number of different shape solutions could be accommodated such that the surgeon can use personal judgment in selecting the best shape solution.

The computer could further customize the output of the bend information. It could minimize the number of bends if desired (for example, with a quicker zigzag type design with greater bend angles at fewer bend points but with potentially greater stress risers). In other embodiments it could increase the number of bend locations to create a smoother design, since the more bend points the smoother the bend. One could limit the program or the device to specific angles so that all angles would be above, at or below a particular value. It could also limit the choices to incremental choices such as every 5 degrees of bend or rotation or distances to a few millimeters. A simple design connecting points could be achieved as could a more complex design as desired. The computer could determine the size of the device, can determine if the attachments means can be adjusted or added to with offsetting devices (and therefore increase or decrease the number of bends to attach the points). In one embodiment, the program can be used to see if the attachment points can be used with a pre-bent device either without modification or with adjustment of the attachment elements or the addition of spatial offsetting devices. The computer could also pick shapes that simplify the shape of the linking device or improve its biomechanics.

A first step in bending a linking device is to determine a bend location. The bend location is a point on the linking device where the bend will occur. It can be measured from a starting point, for example, 1.5 cm from the distal end of a surgical rod, or it can be determined by selecting from a set of fixed points on the device. For example, ruled markings every centimeter on a rod or other device could be marked as point 1, 2; or as 1 cm, 2 cm, etc., and the output of the computer deliver the fixed point. In another embodiment, the device is held in place and moved a given distance from the point held as a reference starting point.

The bend angle is the degrees that the device is bent away from a particular axis or plane. The bend can be accomplished as a single bend or it can be a multiplicity of bends as described above. In general, the bends will be from just greater than zero to 180 degrees off of straight. In many embodiments the bend angle is 90 degrees or less. In general, the maximum bend angle will be determined by a number of factors including the particular use, the surgeon's typical practice, the materials employed and the like. In addition, the angle of rotation off of the direction the device was going could be determined. So, for example, a surgical rod could be angled from zero to 360 degrees off of the zero axis of the original direction of the rod in addition to the bend. Thus a bend of, for example, 45 degrees with a rotation of 15 degrees, 2 centimeters from a starting point could define a particular bend output. The distance rotation and bend angle after determination is then delivered to a computer output. The output can be a paper output, a GUI (Graphic User Interface) or the like, such that a user can read the information and begin the process of bending a device. In one embodiment, the information is delivered directly to the bending device.

Figure 4:
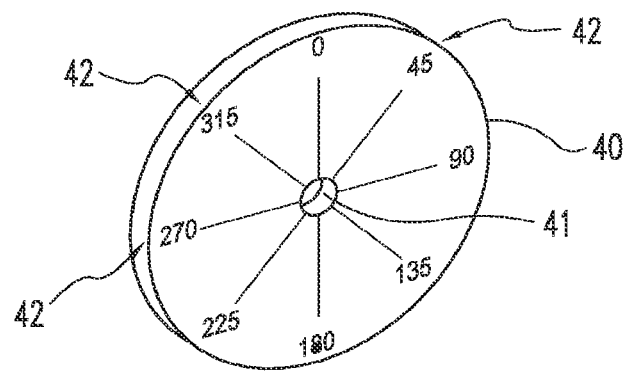
FIG. 4 depicts a front view of a rotation gauge for attaching to a surgical rod.

The means for placing a bend in the surgical linking device can, in one embodiment, be accomplished by one or more manual devices. Hand measuring distance, a rotation disk (as shown in FIG. 4), and then a bending device for bending to an angle could allow the bending with three interactive devices. Likewise, the device shown in FIG. 7 could be used to set all three parameters on one device. For a device that only needs 4 degrees of freedom, the computer needs only produce distance and bend angle and the various devices above either singly or one single device could be used. Rotation in this case could be set at zero. Further, such as in the case wherein the output of the system determines that a pre-bent rod could be used, the output of all of the parameters except distance could be zero. The system could simply determine which linking device that should be chosen, with or without the need to further manipulate the screw locations or add additional offsetting devices. In this case, no bends may need to be made.

Surgically, the method for installing the surgical linking device on a body bony structure using the present invention, in one embodiment, could be started by placing at least two linking device attachment elements on the body structure at desired locations. Then the spatial relationship of the attachment elements could be determined in a digital manner. The digitized information would be transferred to (including calculated by) a computer which determines one or more of the following: one or more of the bend location, bend angle and bend rotation such that upon making the bends the device will fit the installed attachment means; it could also determine that one or more adjustments or additions to the position of the attachment elements could be made so that one could select a preformed or partially preformed device or that a device could be bent with fewer bends or no bends at all to fit the attachment elements. The computer calculates and delivers the information to a computer output. The output could be used to perform one or more functions during surgery, namely selecting a preformed or partially preformed surgical linking device; placing one or more bends as described above in the device or adjusting the position of the attachment elements or placing an addition to the attachment elements. After the proper selection and bending the surgical linking device is attached to the attachment elements.

The advantages and uses of the computerized means for determining the shape of a surgical linking device are several. It allows for the facilitated implantation of preformed whole rods or segments, and the ability to define the size and shape of the component pieces of a multi-component linking device. The linking device can aid a surgeon in the formation of the desired end result rather than the situation as confronted. The linking device can be designed and formed based on the intersection of this desired end result, the current position of the anatomy, and the location of the affixing points. This can be used to control the reduction of fractures and deformities by defining the amount to translation, rotation and or angular correction and altering the shape of a linking device to achieve the result. Further, it can be used to correct spondylolisthesis.

In another embodiment, this method could be used to define the resultant rod and thus help form, obtain and/or hold the correction required in performing an osteotomy or other type of corrective technique used in surgery. The linkage device can be implanted without any static load imparted to the body, or with a predefined load which can aid in adjusting deformities or set the location of a flexible system. One could determine how the anatomy moves or has moved or changed, and one can determine the amount of implant manipulation needed to gain the anatomical change desired. (For example, using x-rays in the OR and comparing them to images taken prior to surgery it is possible to figure out how much to alter the shape of the linkage device in order to achieve the straightness the patient can physically achieve by bending). In one embodiment, one linkage device could be made which would result in completely obtaining the desired end result. In another embodiment, successive intervening steps could be made (i.e.—multiple linkage devices incorporating successively greater amounts of deformity correction) to allow a slower, more gradual correction of the deformity. As all people's anatomy changes to some degree when lying in an OR table versus the upright position, the present invention could be used to account for this change.

Although in one embodiment, the rod can be formed quickly at the time of surgery, this is not required. One could immediately implant or defer the linking device implantation such as to let ongrowth or ingrowth occur then implant the formed rod in a delayed fashion. Further, this system is ideal to custom design large percutaneous implants. As well, it could be used to design a transverse connector that joins two or more linking devices or any other type of implant that could benefit from linking. Further, it can be used to accommodate an easy way to extend the linking device should this be required in the future, as the end configuration and angle of one embodiment of this device is know at the time of production and therefore this additional step (which is useful typically in a delayed fashion months to years later) could further be incorporated.

Bending is preferably accomplished manually at the surgical site by known means but in the alternative can be accomplished with novel devices of the present invention. Novel bending devices all comprise at least one lever, namely in the form of a bar or long arm that can be used to bend an object around a particular pivot point. With one lever the object to be bent is forced with the aid of the lever. In other embodiments, there is a pair of levers that can bend around a fulcrum that is a point or device that will aid in bending the device around.

Devices such as the French Bender have no means for determining any of the bend parameters discussed above when bending a surgical linking device. The present bending device includes means for determining at least two of those parameters. In one embodiment, the two parameters are location and bend angle. In another embodiment, the device measures location, bend angle and bend rotation. Each lever can have a handle disposed at a distal end to aid in grabbing the lever and leveraging it during use.

The means to measure the spatial parameters can measure a continuous location or angle or in other embodiments the measurement means can measure incrementally (i.e., non-continuously). So, for example, the location can measure in half centimeter, one centimeter or other increments, while the angle of bend or rotation could be measured in five degree increments or the like. Continuous measurement or click stop measurement could be used with each measuring means individually or mixed as desired. Greater accuracy may be obtained by continuous rather than incremental movement, but the choice would be up to the user and type of bender device employed.

In addition, the device may be capable of fixedly holding the linking device. In this manner the bending device can use another means to advance the linking device to the next bending location based on the continuous or click stopped measuring means. By fixedly holding the linking device, the measurements can be made accurately from a specific starting point adding a new starting point after each bend or using the original starting point. For example, a bend could be put at one centimeter and three centimeters from a starting point. In another embodiment, a bend is at the starting point and the next bend a fixed distance from the starting point. In another embodiment, by holding the linking device the linking device could be advanced based on ruled markings on the linking device instead of ruled markings on the bending device. Where on the bending device, there could be regular stop positions that are fixed or in the alternative, continuous adjustment of distance.

In general, one of the embodiments of the present invention is the process for producing bends in a surgical linking device which is comprised of two separate processes linked to each other. The first process is the digital process for determining the spatial parameters of one or more bends. The second process is the manual process of shaping a surgical linking device that applies the location, angle and rotation parameters determined in the first process. The complete linking of these two processes is facilitated by the introduction of the novel device of the present invention. The link can be the surgeon or other individual who takes the computer output and applies the result to the linking device, whether manually or by an automated bender or contouring device. For example, in another embodiment, the process or method for the determination of the linkage device, including selection, alteration of fixation points or location, etc., could be applied to any of a host of novel devices which would be necessary to help in the formation of the actual device. This would be ideal as materials used in orthopedic surgery change over time, such as described in U.S. Pat. No. 6,749,614 issued Jun. 15, 2004 to Teitelbaum, et al.

Figure 1B:
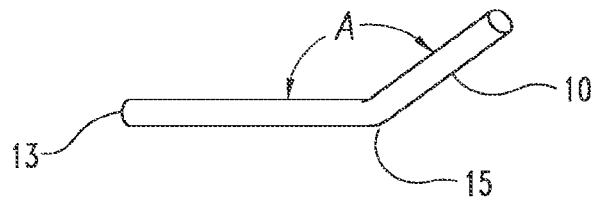
Figure 1C:
Figure 1D:
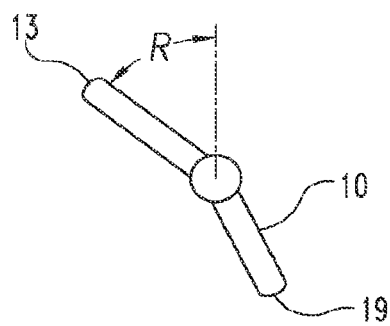

Now referring to the figures, FIGS. 1a through 1d depict various bends in a surgical rod linking device. FIG. 1a depicts a rod with a first bend 11 and second bend 12. This depiction has the rod 10 lying in one plane and the distance between bend 11 and bend 12 is shown as D. By indicating a distance D from bend 11, one can obtain the location of the second bend 12. The starting point for measurement could be either from point 13, the first rod end or bend 11. The starting point for bend location can stay with the original point for subsequent bend location determinations or can move with each bend location determination. So for example, bend 12 could be the starting point for the next bend location determination. In FIG. 1b, a single bend 15 is shown with an angle A. The angle A is the second determined parameter of the present invention. FIGS. 1c and 1d depict a bent rod with at least one bend that has been rotated R degrees from the initial plane of the rod. Second end 19 is also depicted and in FIG. 1d the view is head on to the middle section of the bent rod 10. While a surgical rod 10 is depicted for clarity, a surgical plate or other surgical linking device could also be oriented and bent or shaped in a similar manner.

Figure 2:
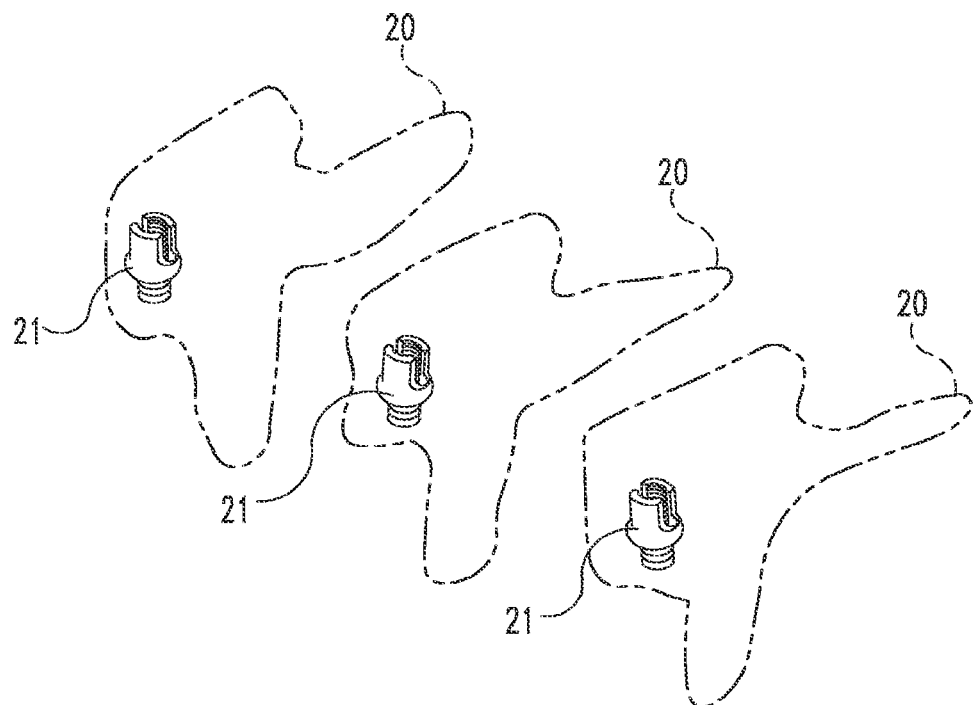
FIG. 2 depicts three vertebrae each with a surgical rod attachment screw.

FIG. 2 depicts body structure vertebrae 20 laid out in perspective view. Each vertebrae 20 has had attachment elements, vertebral screw 21 installed for the purpose of installing a surgical rod. Note that while normally rods are installed in pairs one set of screws 21 is shown for simplicity's sake.

Figure 3:
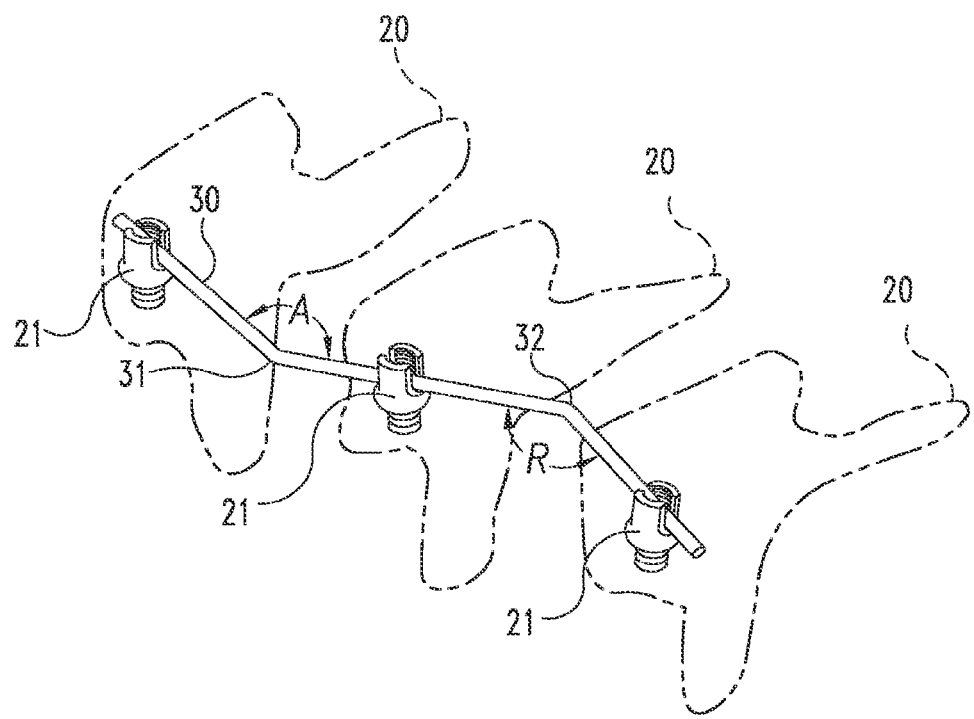
FIG. 3 depicts three vertebrae with a bent surgical rod attached to the three rod attachment screws.

FIG. 3 depicts a bent surgical rod 30 which has been attached to the attachment elements 21. Also depicted is bend angle A and rotation angle R at which the rod has been bent to accommodate the positions of the attachment screws 21.

FIG. 4 is a rotation gauge 40 which may be fitted on the end of or around a surgical linking device, for example, the rod 10 depicted in FIG. 1. The rod 10 fits into hole 41 and then if the rod is rotated to the degree markings 42, a rotational bend of a selected angle can be achieved. This device could be fixedly attached to a bending device as further taught herein.

Figure 5A:
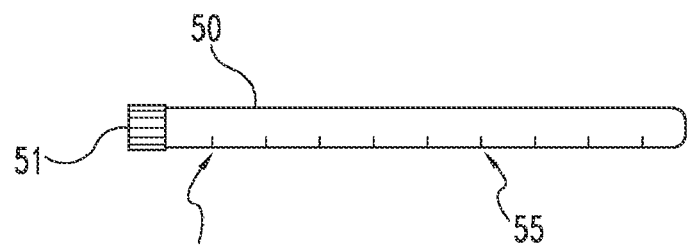
FIGS. 5a and 5b depict surgical rods with ruled markings.
Figure 5B:
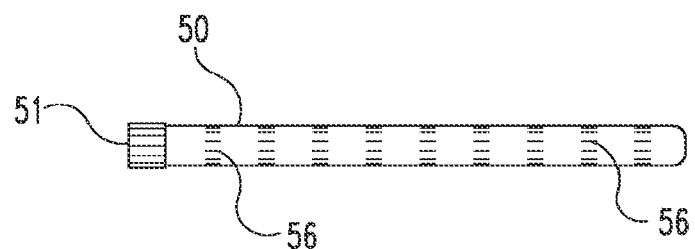

In FIGS. 5a and 5b surgical linking rods 50 are shown. These rods are normally cylindrical but first end 51 is squared off to accommodate a tool or grabbing means or the like. Any number of other end configurations could, in addition, be used that can be firmly held or gripped. The gauge 40 from FIG. 4 could also be attached to this end. These surgical linking rods 50 also show either distance markings 55 to indicate the distance for a bend location. In the case of FIG. 5b rotational markings 56 are available not only for distance measurements but for rotational measurements as well.

Figure 6:
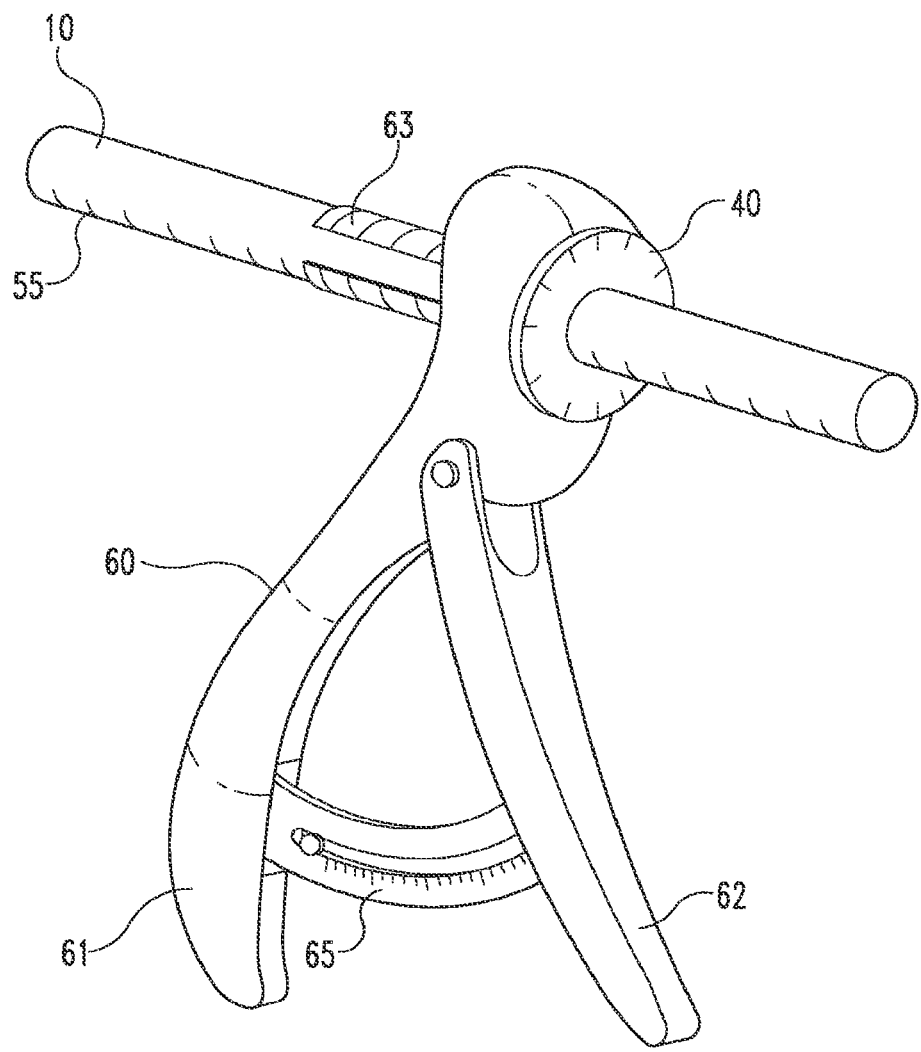
FIG. 6 depicts a small hand device for bending a surgical rod and having a means for measuring location, rotation and angle bend.

FIG. 6 depicts a simple hand bending device 60. By squeezing handles 61 and 62, rod 10 can be bent around a fulcrum (not seen). The rod is not held in place but the rod 10 is moved and by matching distance markings 63 on device 60 with rod distance markings 55 a clear location on the rod 10 can be determined. Rotational gauge 40 is installed and by manually rotating the rod 10 one can obtain a desired rotation. While the rotation is marked in intervals, this embodiment allows free rotation of rod 10 thus infinite rotational angle. The bend angle is measured by angle gauge 65. Angle gauge 65 measures the angle based on how close the handles 61 and 62 approach each other during the operation of bending rod 10.

Figure 7:
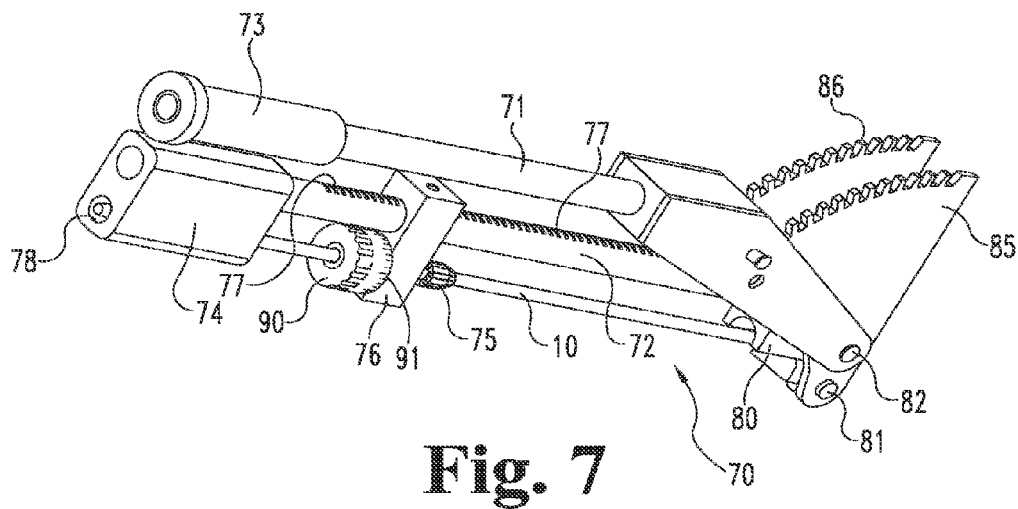
FIG. 7 is a perspective view of a dual lever surgical rod bending device.

FIG. 7 is a perspective view of a more detailed bending device 70 with less manual manipulation of the rod 10. A first lever 71 is shown as is lever handle 73 designed for grabbing the lever 71 manually. Likewise, lever 72 is shown with handle grip 74. Grip 74 has rod pass through 78 so that an infinitely long rod 10 can be used with this particular handle as well as steady the rod during the bending process with bender 70. The user of the device grabs both handles and opens the handles to bend the particular surgical rod 10 by picking an angle on the angle gauge and closing the handles 71 and 72 together. The device in other embodiments could be produced to bend the rod during the handle opening movement as well. The rod 10 moves through mandrel 80 and in between moving die 81 and fixed die 82. A better view of the dies is in FIG. 10. The surgical rod is bent between the two dies 81 and 82. Gauges on the device allow the user to manipulate the surgical 10 rod in order to determine bend position, bend angle and bend rotation. The surgical rod 10 is held in place by collet 75. By sliding slide block 76, along handle 72, the surgical rod 10 can be moved proximally and distally in the bending device 70. Position is measured by click stops 77 at regular intervals along handle 72. Each click stop 77 is a measured distance along the handle 72 and thus moving a specific number of click stops 77 gives one a precise location for the location of a surgical rod 10 bend.

The bend angle is measured by using angle gauge 85. Gauge 85 has ratchet teeth 86 spaced at regular intervals. Each ratchet stop represents five degrees of bend angle. Thus the user can bend a surgical rod 10 in five degree increments with the particular bend angle gauge 85 as the handles 71 and 72 are opened and closed. The bend rotation is controlled by a dial in the form of collet knob 90. By rotating collet knob 90 either clockwise or counterclockwise the user can set a particular rotation angle. The collet knob 90 is marked with regular interval notches 91 but this particular embodiment is continuously turn able and thus has infinite settings. Once a user turns knob 90 the user can set the knob 90 at a particular marking 91 or in between or the like to determine a particular angle rotation to a high degree of accuracy.

In this particular embodiment, once the rod 10 is locked in place with collet 75 if there is enough room on the lever 72 to move the slider 76 distally or proximally then the rod 10 can remain fixedly attached to collet 75. Should a longer area need to be bent, then the rod 10 can be unlocked moved and relocked and measurements start from the new position. Merely adding the positions together using the information supplied by the computer output would be an easy task with the present invention.

Figure 8:
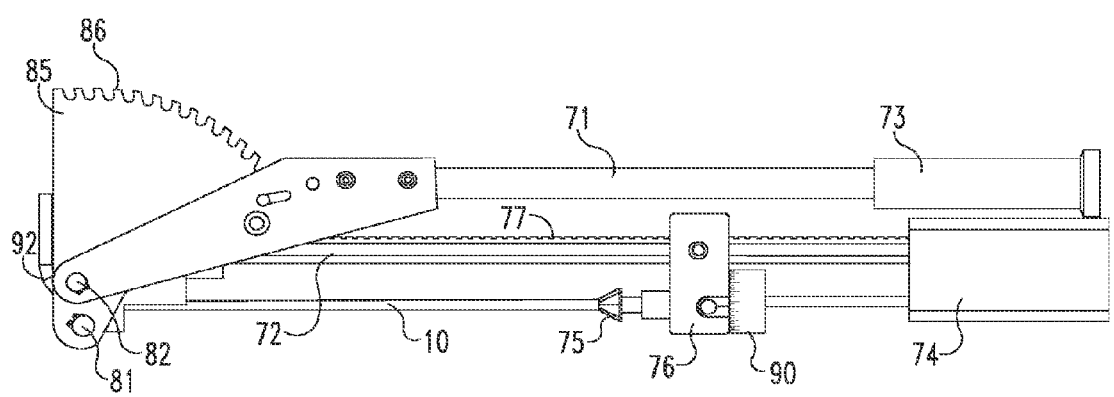
FIG. 8 is a side view of a dual lever surgical rod bending device.
Figure 9:
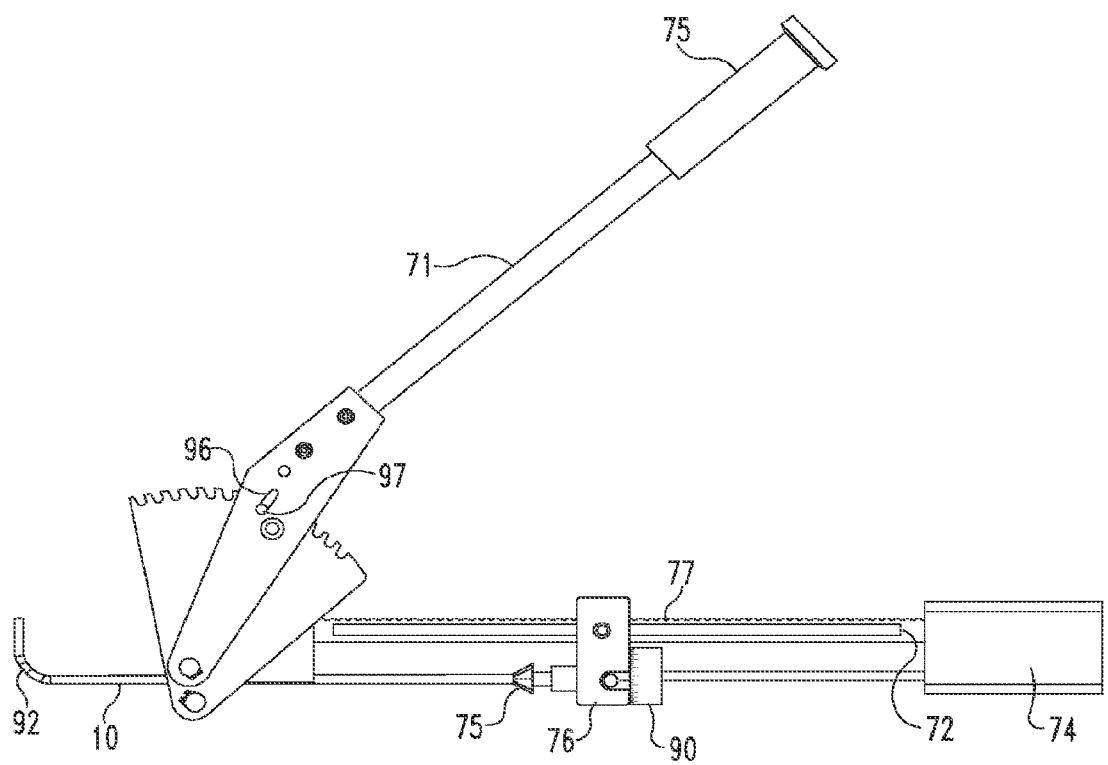
FIG. 9 is a view of a dual lever surgical rod bending device with the levers in the open position.

FIG. 8 depicts the bending device 70 in a side view. In this view one can clearly see the rod 10 has bend 92. FIG. 9 shows a side view wherein handle 71 is open in preparation of making a second bend in rod 10. Bend gauge window 96 shows bend angle pin 97 which has engaged 2 teeth 86 in preparation for placing the second bend. As can be seen in this view the rod 10 has moved distally since slider 76 is in a more distal position than shown in FIGS. 7 and 8. First bend 92 has moved distally as well and upon closing of levers 71 and 72 a second bend will be placed in rod 10.

Figure 10:
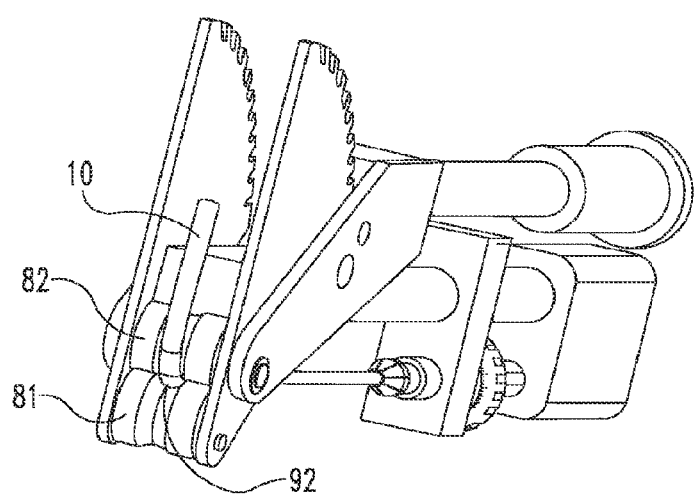
FIG. 10 is an end on perspective which allows view of the fulcrum means.

FIG. 10 shows a head on view of the device 70. In this view, the rod 10 can clearly be seen in bent position between moving die 81 and fixed die 82. The moving die 81 allows for free movement of rod 10 and the fixed die 82 allows for relatively easy bending of rod 10.

Figure 11:
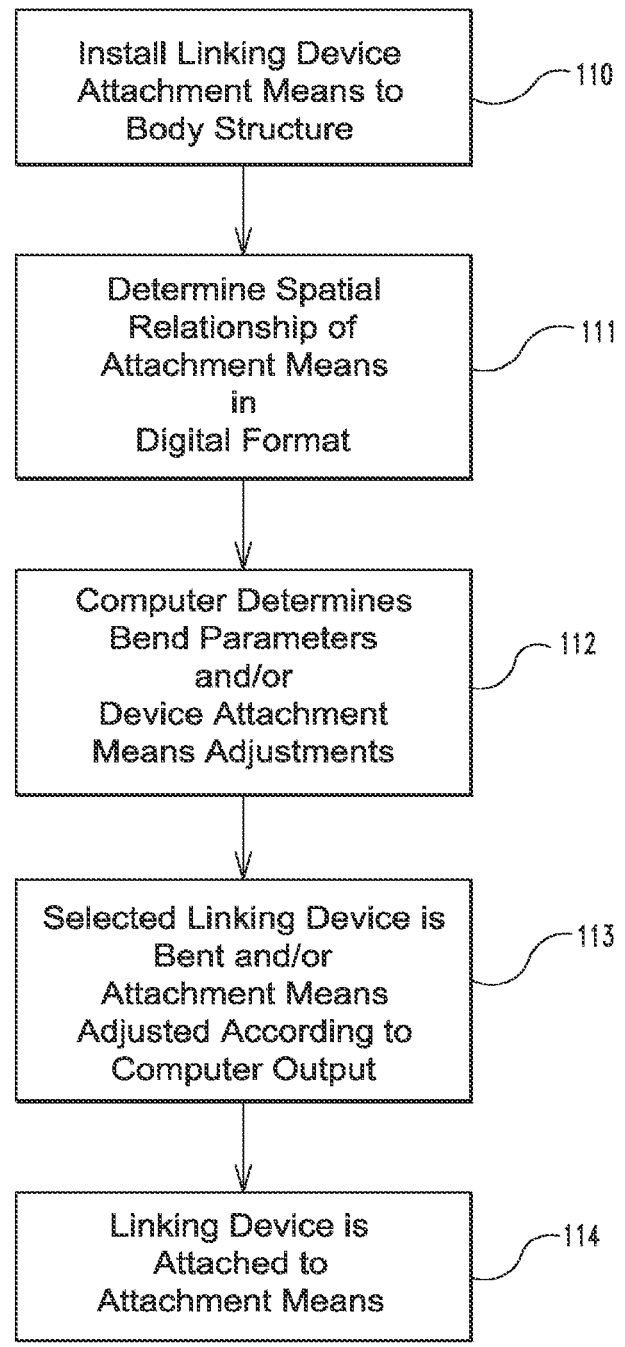
FIG. 11 is a flow diagram of an embodiment for determining bend information.
Figure 12A:
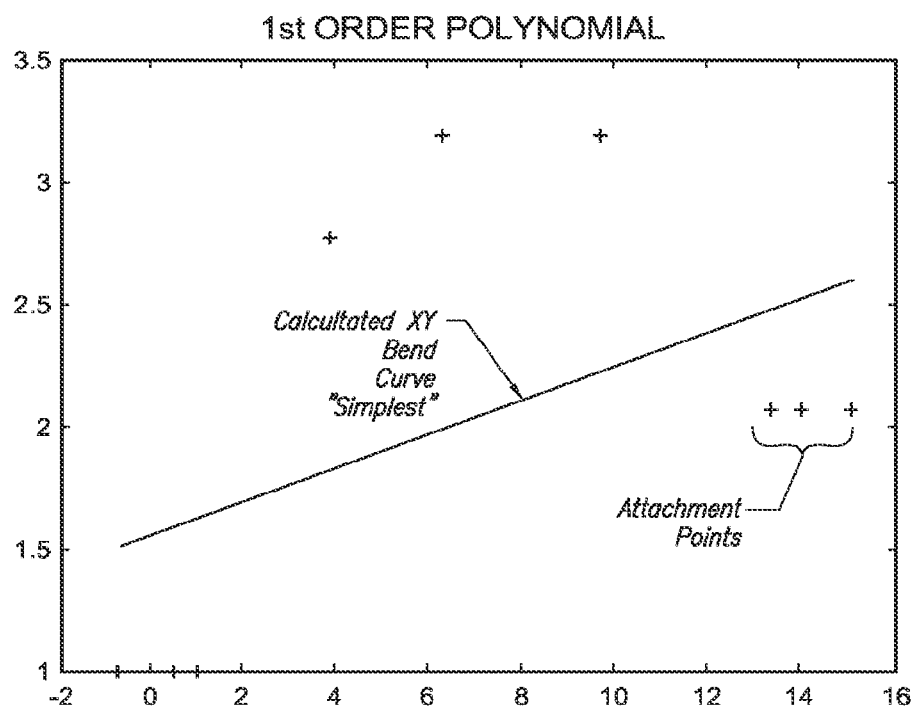
FIGS. 12a-h show a comparison between the IdealScrewPositions in the XY (coronal) plane for an exemplary implant and the calculated positions according to one example of the curve fitting approach of the present invention.
Figure 12B:
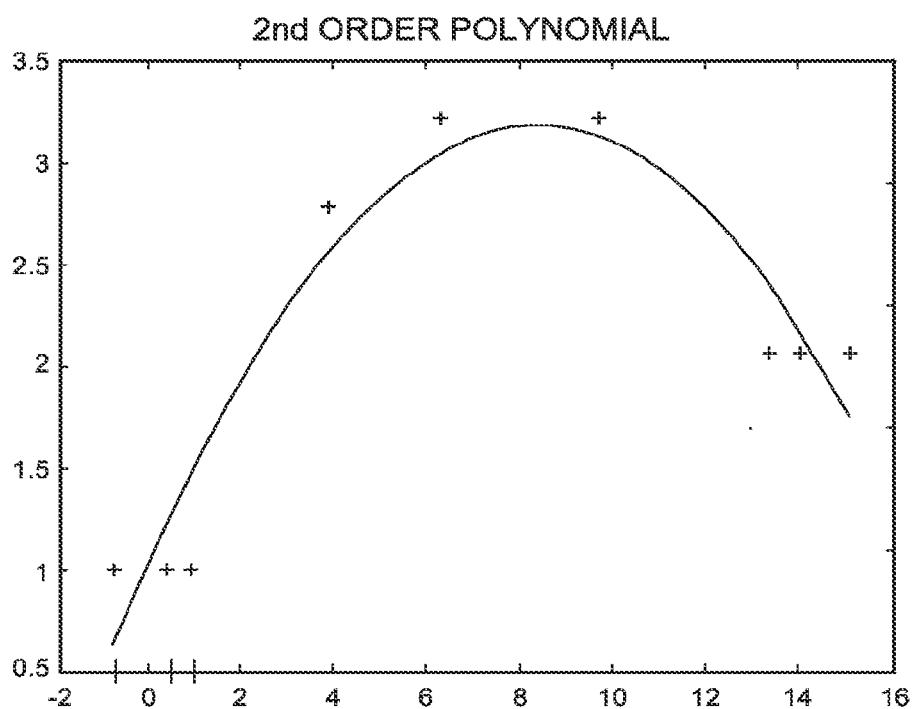
Figure 12C:
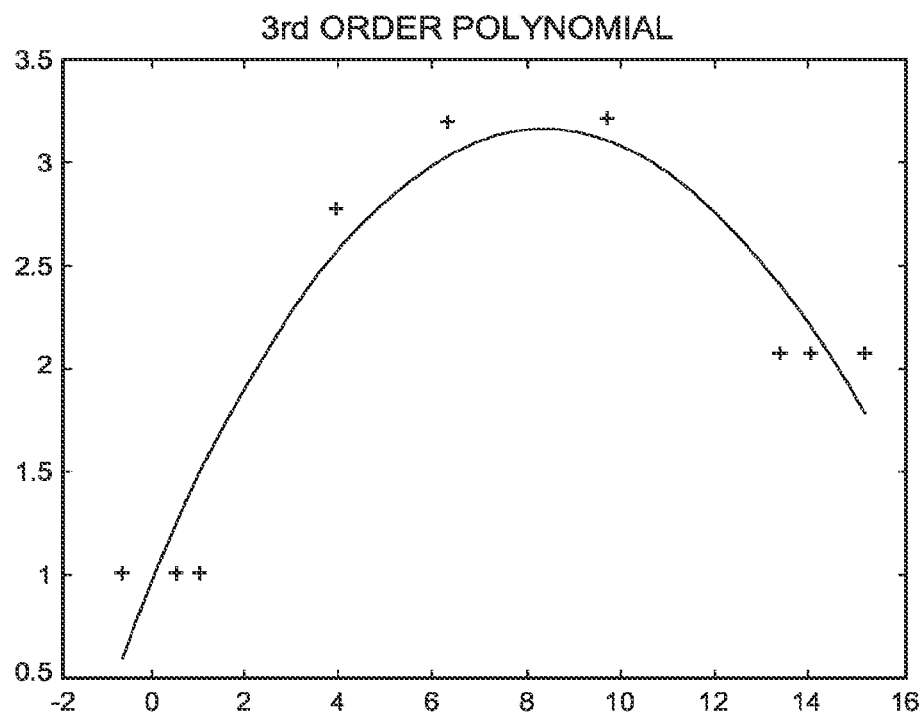
Figure 12D:
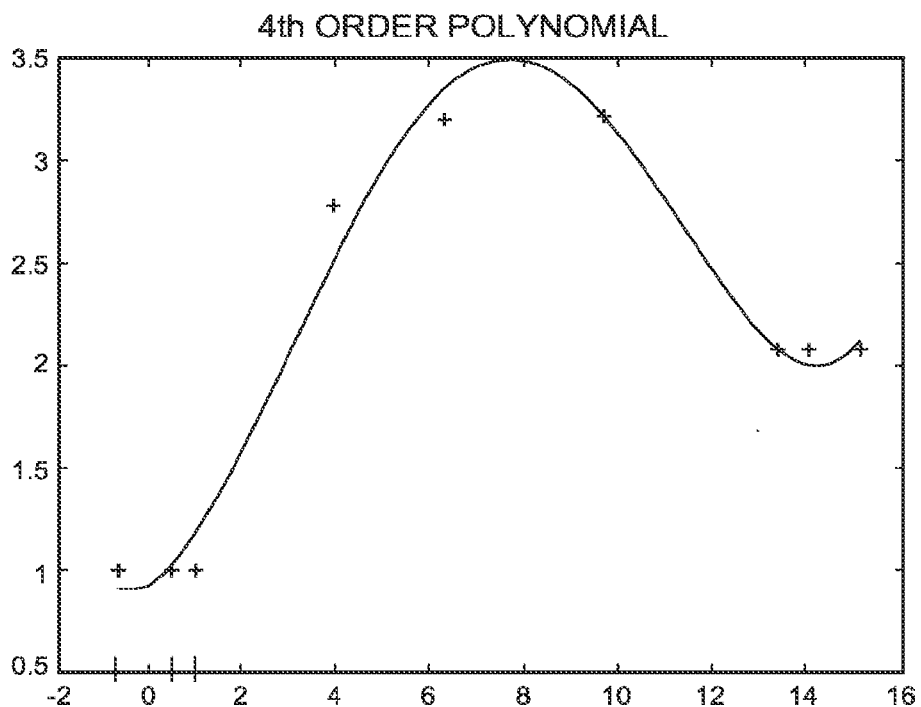
Figure 12E:
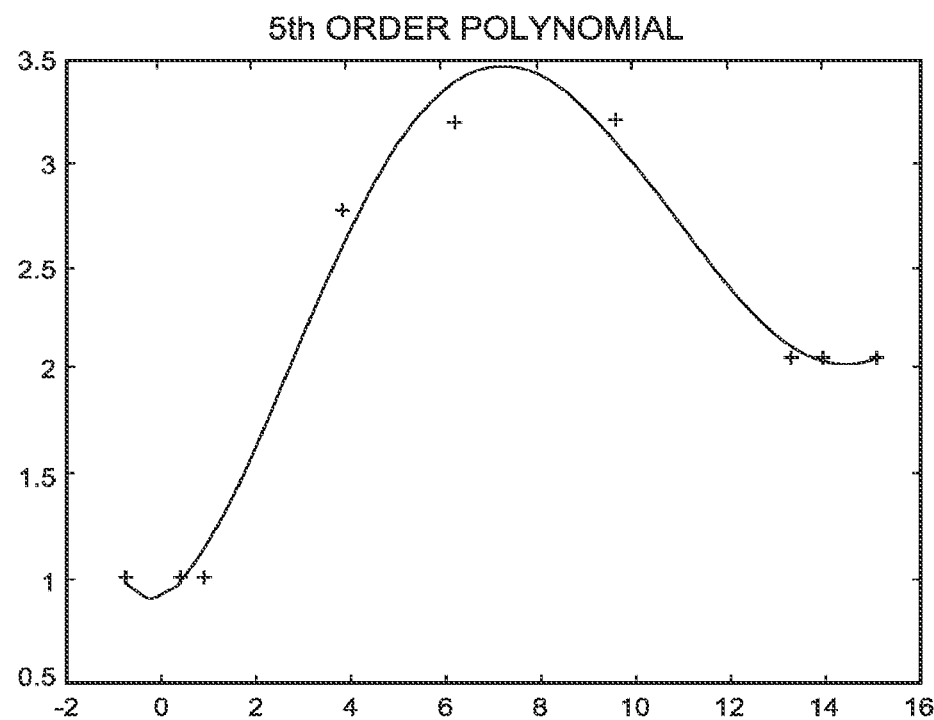
Figure 12F:
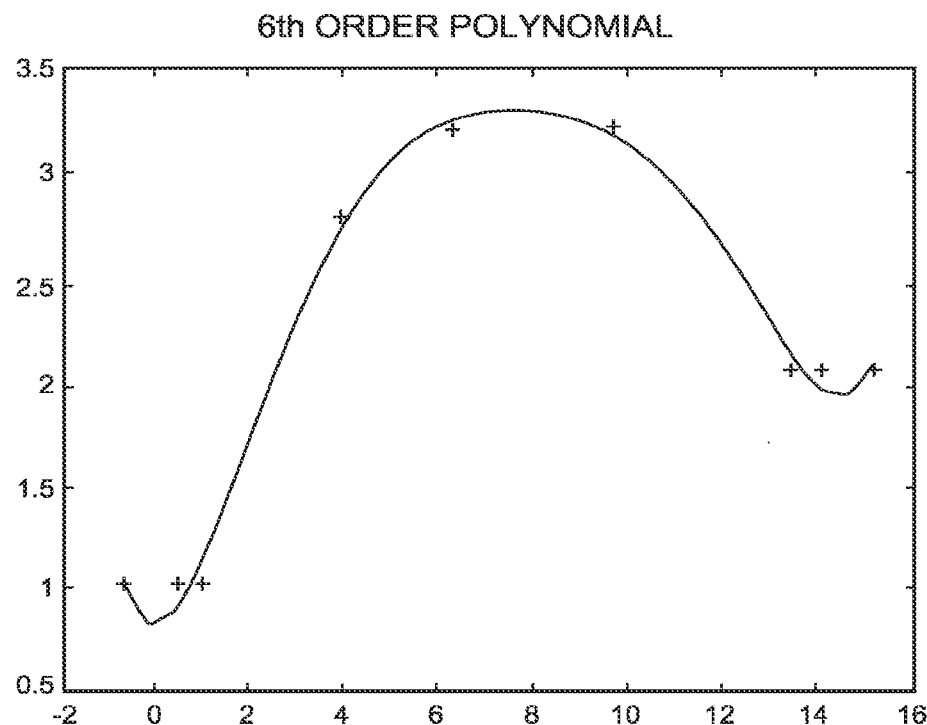
Figure 12G:
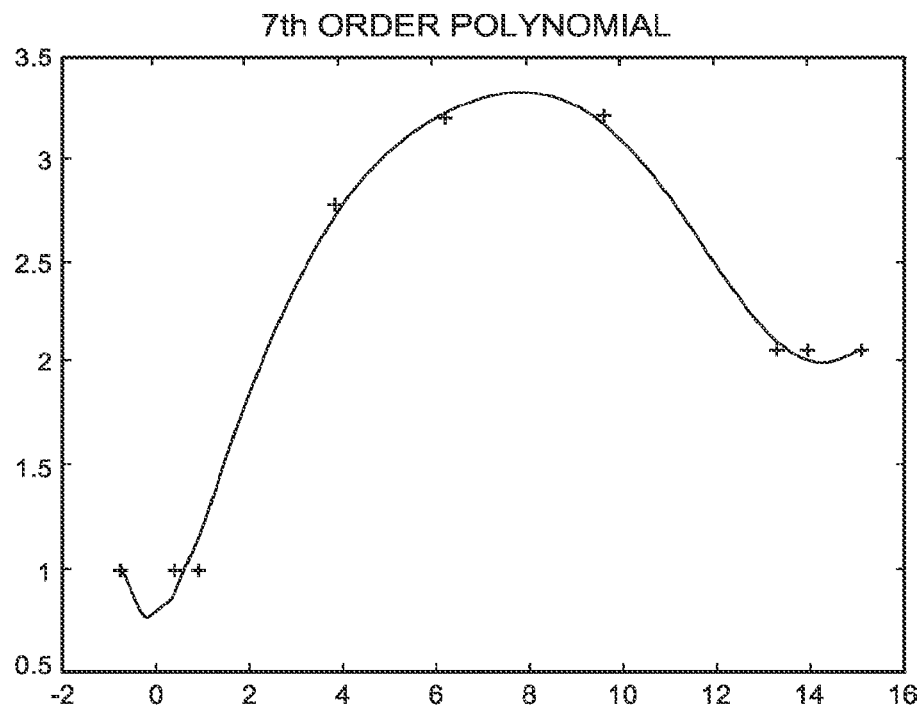
Figure 12H:
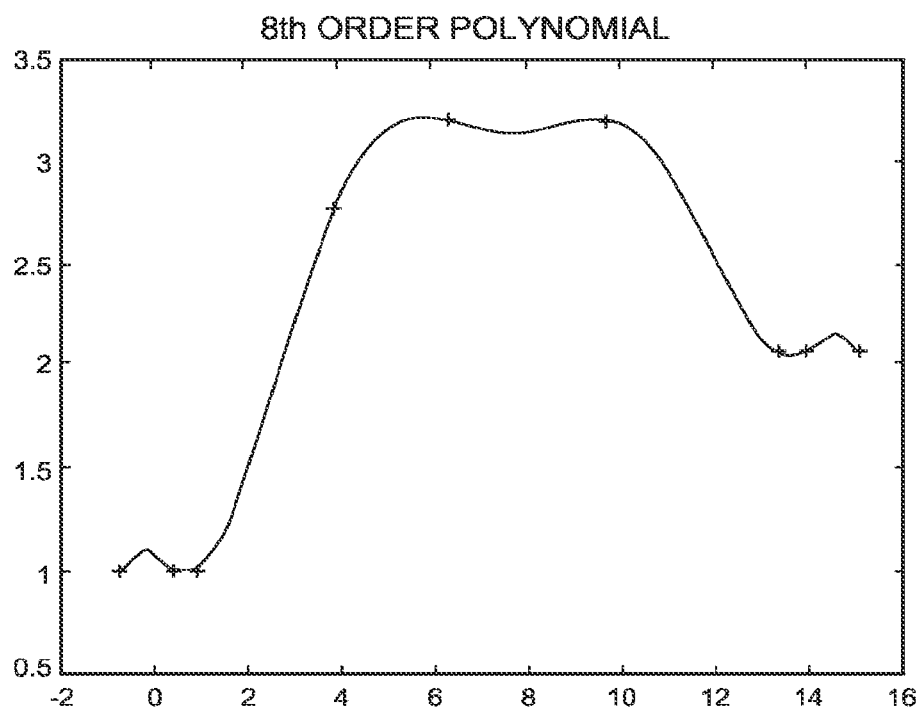
Figure 13A:
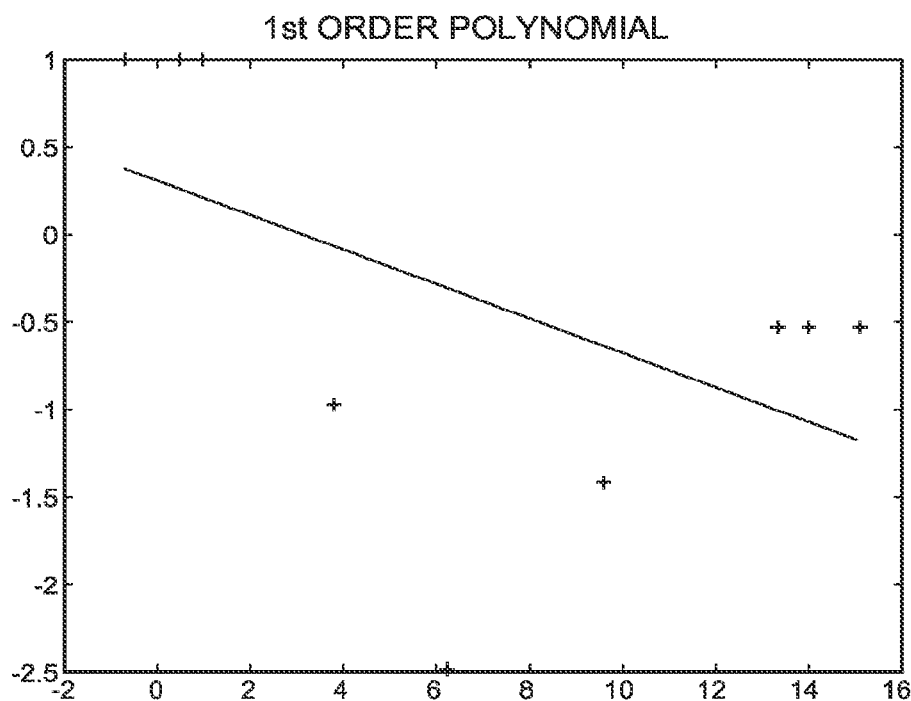
FIGS. 13a-f show a comparison between the IdealScrewPositions in the XZ (sagittal) plane for an exemplary implant and the calculated positions according to one example of the curve fitting approach of the present invention.
Figure 13B:
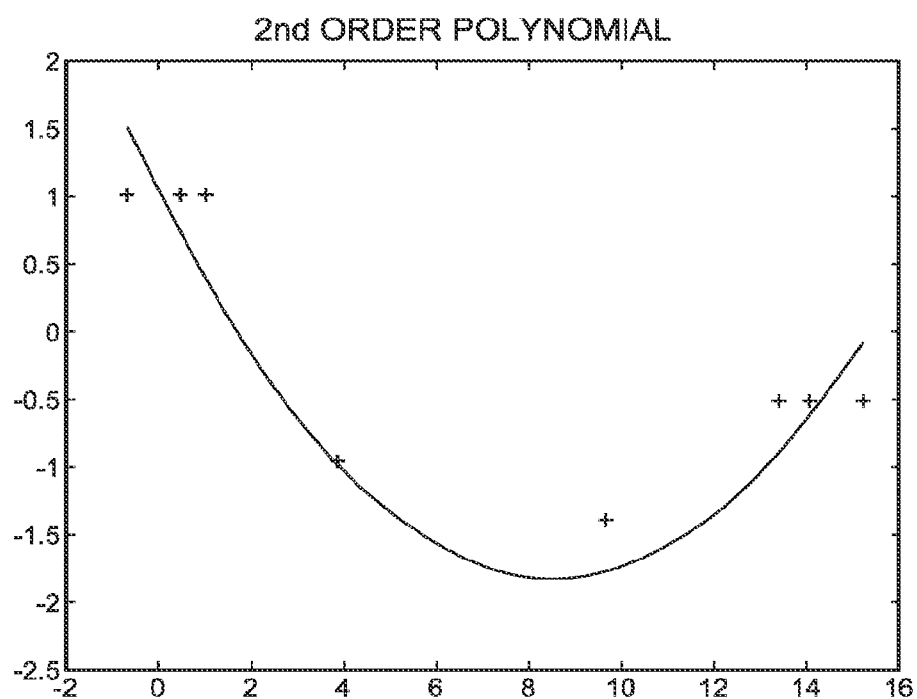
Figure 13C:
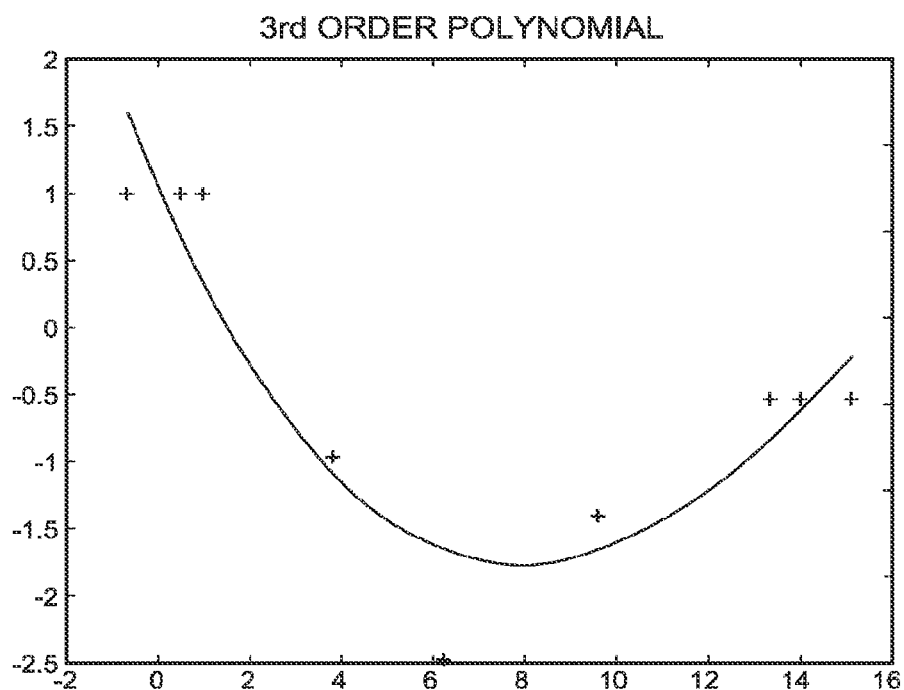
Figure 13D:
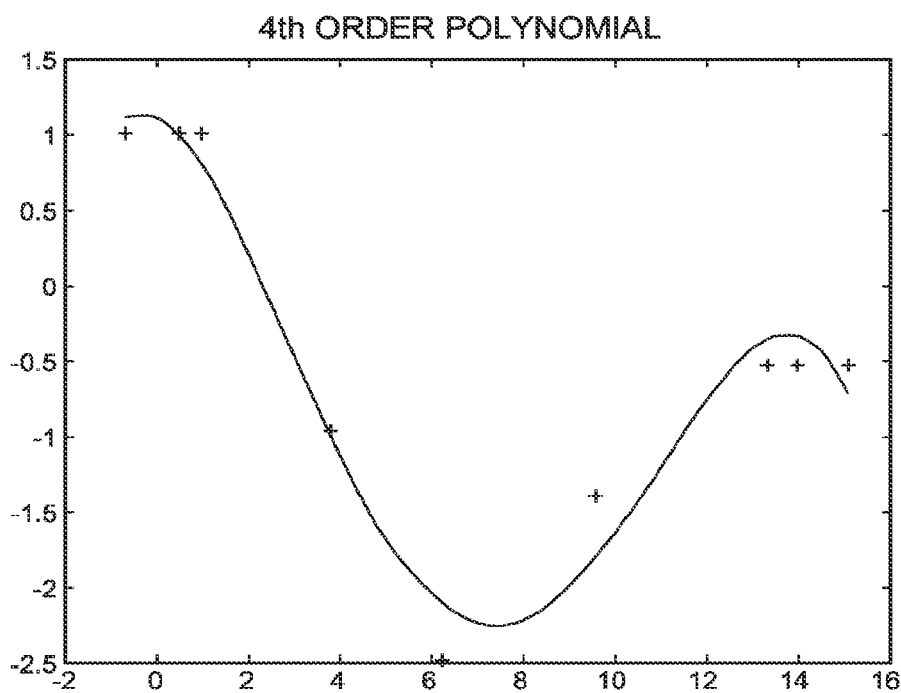
Figure 13E:
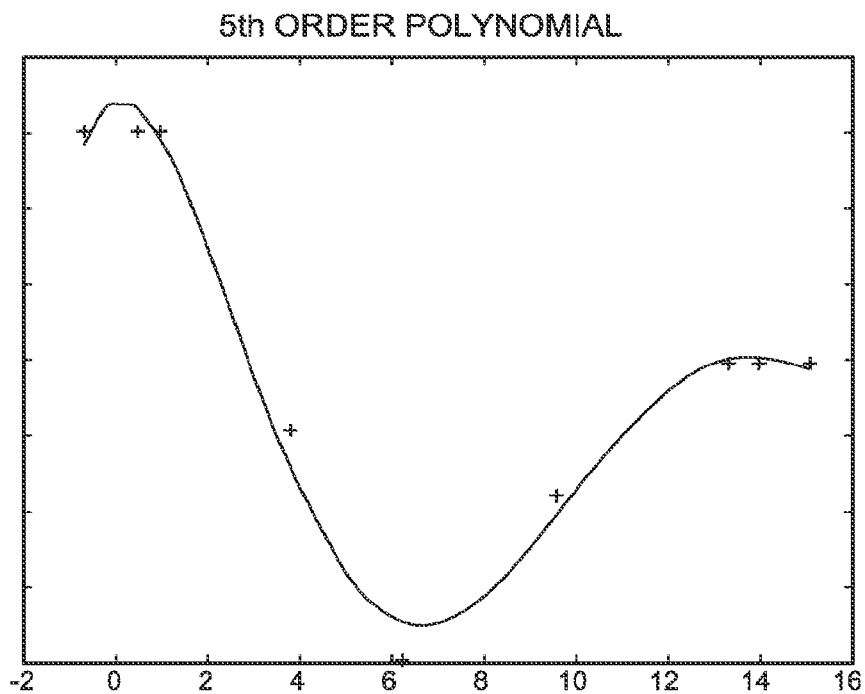
Figure 13F:
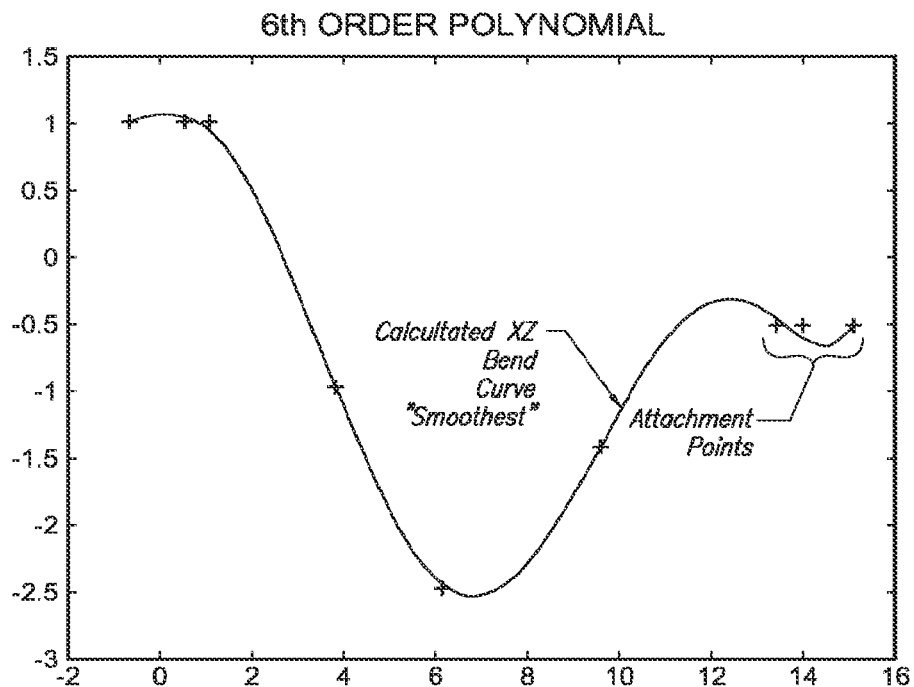

FIG. 11 depicts a flow chart of a particular embodiment of the operation of the computer means in combination with the device of the present invention. The first step 110 in the process is the installation of a linking device attachment elements to a body structure. In other embodiments, for example for use with a surgical plate, the first step is to determine the surface spatial relationship of the bony structure and then using that spatial information to determine the shape of the surgical plate. Once the plate is placed on the bony structure attachment means are positioned through the plate and into the bony structure. The linking device such as screws for use with surgical rods, which to some degree adjustable then determines where the linking device will be positioned.

The next step 111 is the determination of the spatial relationship of the attachment elements into a digital format. This is done not only taking into account the position of attachment, but also taking into consideration any body structures which may intervene in the process. It would not be useful if a part of the vertebrae were in the way of a particular bend solution because the resulting bent rod would not fit the attachment points because of body structure interference. One skilled in the art could easily make the appropriate adjustments to the computer calculation based on the disclosure herein.

Next, the computer with the possession of the digital format determines the bend parameters and or the device attachment elements adjustments in step 112. This step may also include the selection of a particular linking device, the size it needs to be, or to select from a list of pre-bent linking devices. Once a linking device is selected from the computer output parameters, the linking device is then, if necessary, bent or shaped and or the attachment elements adjusted in step 113. After the appropriate bends have been made, the linking device is attached to the attachment elements in step 114.

Step 112 of the flowchart of FIG. 11 entails first determining a mathematic representation of a linking device (such as a rod or a plate) that will fit each of the attachment means in situ. Thus, according to one embodiment, a software program implements a curve fitting algorithm that is adapted to approximate a smooth curve spanning between the attachment points, with the curve falling within an acceptable error at the location of each attachment point. The software program starts with the digitized data establishing the three-dimensional position of each attachment point. In order to simplify the curve fitting protocol, the present invention contemplates that the three-dimensional data are used to establish the attachment points in two orthogonal planes—the sagittal or XZ plane, and the coronal or XY plane. As is known in this field, the sagittal plane corresponds to a vertical plane passing through the spine from the front to the back of the patient. The coronal plane is perpendicular to the sagittal plane and extends side to side through the patient. The division of the 3D coordinate system into two 2D planes may be used in one embodiment as described in detail herein, but would not be required for the functioning of the system. In another embodiment, a single 3D curve fitting program is employed.

It is thus an object of the software program to derive a curve in each plane that fits the actual position of the attachment points in situ. In most cases, the curves in the sagittal and coronal planes are complex, meaning that the curves will typically incorporate multiple inflection points. Thus, it should be understood that a straight line or even an arcuate line will usually be inadequate to fit the true position of the attachment points, especially as the number of attachment points increase. It can be appreciated then that a first or second order polynomial expression for a curve in either plane will rarely be sufficient to model the three-dimensional representation. It can be further appreciated that an exact curve fit is unlikely, even if the polynomial is extended to a very high order.

The present invention accounts for these difficulties by incorporating an acceptable error between the actual three-dimensional location of an attachment point and its mathematical representation. This error is acceptable if kept within certain constraints because of the ability of the surgeon to manipulate the linking device, inherent characteristics of the attachment points and linkage device and even the spine when completing the spinal construct. For instance, where the attachment point is a bi-axial or multi-axial bone screw, the head of the screw can be toggled or pivoted so that the rod-receiving channel of the screw can be oriented to receive a linking device, such as a spinal rod. In addition, in many attachment devices, the interface point is the channel of a yoke or saddle-shaped structure, which provides variability to the angle between the rod and the head of the bone screw. In some devices the screw permits variation in vertical orientation relative to the bone. Each of these factors contributes to an acceptable error or tolerance. Other factors that may be considered in deriving the acceptable error include the material of the bone screw and the liking device, the cross-sectional shape of the linking member, the distance between attachment points, and the size of the bone screw and the linking member.

In accordance with the dual plane approach of the present embodiment, the error, or more appropriately tolerance, is established in each plane. For illustration purposes these tolerances can be designated ToleranceXY and Tolerance XZ. The ToleranceXY in one embodiment can be given by the expression:

$$\text{Tolerance}XY = \tan(0.5 * \text{MaxHeadAngle}) * (\text{distance from the end of the fixed shaft of the screw to the ideal rod location}).$$

The term "MaxHeadAngle" corresponds to the maximum angle through which the head of a bone screw can toggle or pivot. For a typical polyaxial screw, that angle can be in the range of 50°. The last term in the expression essentially corresponds to one side of a triangle indicating the depth of the saddle of the screw that can accommodate the linkage device.

The ToleranceXZ corresponds to the inherent amount of vertical translation that the screw head can accommodate.

For example, a screw head having a deep yoke channel, the vertical translation may be as much as several millimeters and in some systems, especially in those in which the heads resemble posts, the number can be much more.

The two tolerance values, ToleranceXY and ToleranceXZ, are determined for each attachment point—i.e., for each bone screw. The tolerance values provide the measure for determining whether a particular polynomial representation of the rod shape is sufficient. Again, these tolerance values may take into account all or some of the factors discussed above.

In accordance with one aspect, the curve approximation for each plane starts with a first degree polynomial, the lowest order possible, and proceeds to increase in order until a curve is developed that satisfies all of the tolerance values. Thus, an initial approximation for a curve fit starts with the equation:

$y=P_i{}^*x^1+P_2$, where $x$ and $y$ define the location of the curve in the coronal or lateral plane with $y$ representing the left to right location of the curve function and $x$ corresponding to the head to foot location along the length of the spine, and $P_i$ are coefficients.

A similar relationship is applied to find the value of z, namely the location of the curve in the sagittal, or front-to-back-plane. Further, in other embodiments of the present invention, other curve fitting algorithms are used to establish an equation for the linking device, all increasing in their complexity as they minimize the error between the determined curve and the attachment points.

Invariably, this first order polynomial will be insufficient to provide a curve linking all of the attachment points. The order of the polynomial is then successively increased according to the following equation:

$y=P_1{}^*X^N+P_2X^{N-1}+\ldots+P_NX+P_{N+1}$.

For each N-th order polynomial, the error in the two planes (XY and XZ) is calculated using a least squares approach. To determine this error, an IdealScrewPosition value is obtained for each attachment point, namely (Xscrew, yscrew, Zscrew), which corresponds to the ideal location of the spinal rod within the head of the screw. In one embodiment, the Ideal Screw Position values may correspond to the digitized data for each screw in situ, in a manner as described above. In accordance with one aspect of the invention, the two errors ErrorXY and ErrorXZ are defined by the distanced from the calculated curve function to the IdealScrewPosition at two points on either side of the Ideal Screw Position according to the following relationships:

$$ErrorXY = \frac{(x_{curve2}-x_{curve1})^*y_{screw}+(y_{curve2}{}^*x_{curve1}-x_{curve2}{}^*y_{curve1}))}{((x_{curve2}-x_{curve1})^2+(y_{curve2}-y_{curve1})^2)^{1/2}}$$

$$ErrorXZ = \frac{(x_{curve2}-x_{curve1})^*z_{screw}+(z_{curve2}{}^*x_{curve1}-x_{curve2}{}^*z_{curve1}))}{((x_{curve2}-x_{curve1})^2+(z_{curve2}-z_{curve1})^2)^{1/2}}$$

If any of these error values exceeds the tolerance values (ImplantToleranceXY or ImplantToleranceXZ), then the order of the polynomial is increased and the least mean squared function and error calculations are re-run. In some embodiments, the tolerance values are augmented by some small dimension, for instance 1 mm, to help simplify the curve function and therefore eliminate bend points when the final bend curve is created. In other words, it is typically desirable to reduce the number of bends that are needed to fit the implant locations, especially when performed manually. When applied otherwise, for example in embodiments using non-manual bending devices or alternative materials that benefit from, reducing the number of bends may not be required or considered as advantageous to achieve a very smooth result. The augmented tolerance values can eliminate some bends that might otherwise arise with a tightly toleranced curve calculation.

In another aspect of the inventive procedure, steps may be taken to ensure that the rod interaction with the head of the screw falls within a predetermined angle. This predetermined angle is based on the value MaxHeadAngle, which is described above as the maximum permissible angle through which the head of the fastener/screw may toggle. It can be determined that the angle at which the rod crosses the head of the screw is defined by:

Rod2ScrewAngle=arc sin($V_{screw} \bullet V_{rod}$), where the operator "•" signifies the dot product of the two vectors corresponding to the orientation of the screw and the approach angle of the rod.

In circumstances in which the rod crosses the head of the screw too acutely (i.e., outside the boundaries set by MaxHeadAngle), the generated curve is altered in the immediate region of the screw using a segmental rod morphology which crosses within the correct range. Specifically, the curve function is altered by an amount R so that the Rod2ScrewAngle function is equal to half the value of MaxHeadAngle. In other words, $V_{required\ rod}=V_{rod}+(R \times V_{screw})$, and ($\frac{1}{2} \times$MaxHeadAngle)=arc sin($V_{screw} \bullet V_{required\ rod}$).

The curve is then altered across the small segment adjacent the particular screw as follows:

$D=V_{required\ rod} \times (x_2-x_1)$;

$y_{1\ new}=y_1+D$ $y_{2\ new}=y_2-D$.

It is also contemplated that in using the least mean square approach described above to determine the rod curve, some regions of the resultant rod may conflict with the surrounding anatomy. In extreme situations, this competition can be eliminated in part by simply defining any anatomical points of concern at the same time that screw positions are determined. In other words, the anatomy that must be avoided can be defined ab initio along with the locations of the several bone fasteners/screws.

However, in the typical case, no strange anatomy is encountered. In this instance, it is common for the bone fastener head to project from the bony anatomy in to which it is anchored by a certain distance, usually about 1 cm. When the bend curve is defined, all that is required is that the resulting rod position fall within a "safe region" which can be pre-defined as a few millimeters above and below a straight line connecting successive IdealScrewPositions. When the curve function would result in the calculated rod position falling outside this "safe region", the curve is altered towards the straight line. In one specific embodiment, if any point along the calculated curve that extends above a line defined by the slope M of a line connecting screws at positions ($x_{screw1}$, $y_{screw1}$, $z_{screw1}$) and ($x_{screw2}$, $y_{screw2}$, $z_{screw2}$) exceeds a specified amount, the whole section of the curve ($x_{curve1}$, $y_{curve1}$, $z_{curve1}$) to ($x_{curveN}$, $y_{curveN}$, $z_{curveN}$) between the two screw positions is brought closer the straight line. Thus, $$M=(z_{screw2}-z_{screw1})/(x_{screw2}-x_{screw1}); \text{ and}$$

$$Z_{curve}(1 \text{ to } N)=\tfrac{1}{2}\times(z_{curve}(1 \text{ to } N)+z_{curve1}+[0 \; M \; 2M \ldots (N-1)M]).$$

In yet another embodiment, additional smoothing functions may be applied to further smooth the overall shape of the resultant linkage device.

By way of example, FIGS. 12a-h show the sequence of curve fitting polynomials according to one embodiment of the invention, compared to the ideal screw positions of a desired implant construct. The curve fitting for the coronal or XY plane follows the equation: $y=P_1{}^*x^N+P_2{}^*x^{N-1}\ldots P_N{}^*x+P_{N+1}$. According to the specific embodiment, the coefficients for each successive order of the polynomial are:

| | | | | | | | | |
|---|---|---|---|---|---|---|---|---|
| 1$^{st}$ Order | 0.0692 | 1.5576 | | | | | | |
| 2$^{nd}$ Order | −0.0315 | 0.5285 | 0.9663 | | | | | |
| 3$^{rd}$ Order | 0.0003 | −0.0374 | 0.5573 | 0.9579 | | | | |
| 4$^{th}$ Order | 0.0007 | −0.0199 | 0.1381 | 0.1302 | 0.9334 | | | |
| 5$^{th}$ Order | 0.0000 | 0.0021 | −0.0374 | 0.2179 | 0.0385 | 0.8989 | | |
| 6$^{th}$ Order | 0.0000 | −0.0008 | 0.0133 | −0.1119 | 0.4007 | 0.0014 | 0.8104 | |
| 7$^{th}$ Order | 0.0000 | 0.0001 | −0.0024 | 0.0282 | −0.1744 | 0.4974 | 0.0174 | 0.7641 |
| 8$^{th}$ Order | 0.0000 | 0.0001 | −0.0018 | 0.0214 | −0.1312 | 0.3593 | −0.1697 | −0.1664 | 1.0883 |

The polynomial expression for the curve fitting in the sagittal or XZ plane is the same as that given above the XY plane, with the substitution of the variable z in lieu of the variable y. For the specific example, the comparison of the calculated curve to the ideal screw position is shown in FIGS. 13a-f and incorporates the following coefficients for the XZ curve polynomials:

| | | | | | | |
|---|---|---|---|---|---|---|
| 1$^{st}$ Order | −0.0979 | 0.3041 | | | | |
| 2$^{nd}$ Order | 0.0395 | −0.6738 | 1.0455 | | | |
| 3$^{rd}$ Order | −0.0010 | 0.0603 | −0.7752 | 1.0749 | | |
| 4$^{th}$ Order | −0.0011 | 0.0295 | −0.2050 | −0.1293 | 1.1120 | |
| 5$^{th}$ Order | 0.0001 | −0.0049 | 0.0769 | −0.4205 | 0.1183 | 1.2052 |
| 6$^{th}$ Order | 0.0000 | −0.0012 | 0.0148 | −0.0548 | −0.0972 | 0.0526 | 1.0486 |

It can be noted that the curve approximation for the coronal XY plane required an 8$^{th}$ order polynomial, while the approximation for the sagittal XZ plane only required a 6th order polynomial. It should be understood that the order of the polynomial necessary to closely approximate the ideal screw positions in the two planes will frequently be different.

Figure 14:
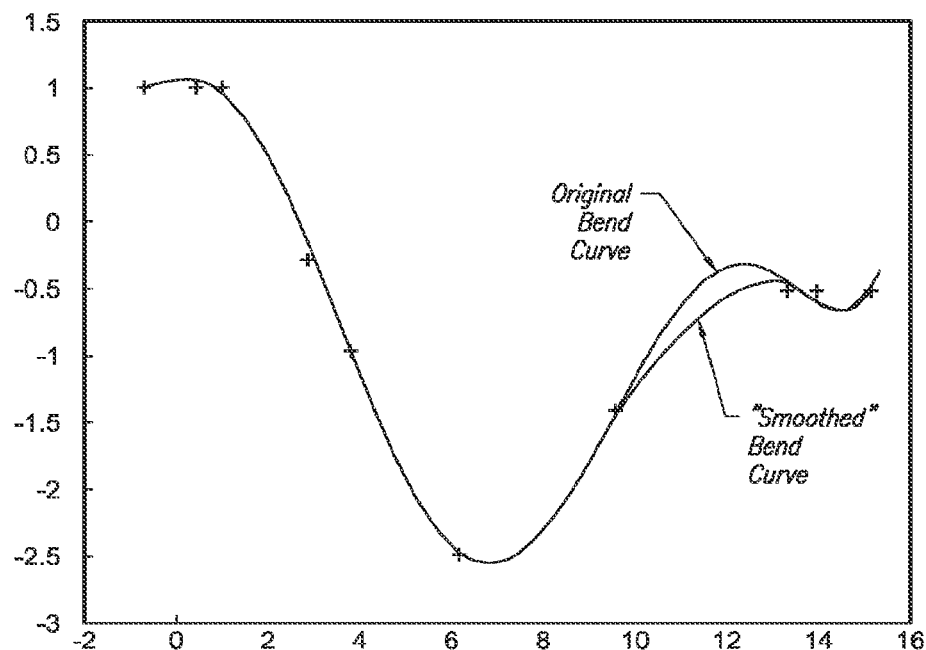
FIG. 14 shows a comparison between a calculated bend curve and a the curve after "smoothing" according to one aspect of the present invention.

For the XZ curve, FIG. 14 illustrates the effect of curve smoothing described above. In particular, in the region of the curve between the screw location 9.5 and last screw location 15.0, the calculated curve provides a suitable contour to fit the four screws in that region. However, the curve segment between the screw locations 9.5 and 13.0 are more exaggerated than necessary—i.e., the calculated curve falls well outside the "safe region" around a straight line through the four locations. Similarly, the curve segment between the penultimate and last screw locations is slightly more exaggerated than necessary.

Thus, using the curve smoothing approach described above, the curve between the first two screw locations is flattened significantly, while the curve between the last two screw locations is flattened slightly. In both cases, the resulting smoothed curve more closely follows the slope M of a line segment passing through the four screw locations.

With the smoothed curve approximations for the XY and XZ planes, the next step is to determine where and how to bend a straight rod to achieve the desired shape. According to one aspect of the present invention, a computer-based system is provided that generates a sequence of bend instructions. In the preferred embodiment, these instructions are adapted to the particular bending tool, such as the tool 70 described above in connection with FIGS. 7-9. Thus, in the illustrated embodiment, the system of the present invention produces a list of bends identified by axial location along the rod, the amount of rotation about the axis of the rod, and the magnitude of the bend.

In order to accommodate the bending tool, the system of the present invention seeks to break down the curve function generated above into manageable line segments that can be readily handled by the bender. Of course, each bending tool has its own inherent tolerances regarding the nature of the bends that it is capable of making. For instance, some bending tools can only make bends in a rod that are separated by 1-2 cm. In accordance with the present illustrate embodiment, the bending tool can accept bends in ½ cm increments. Thus, the software of the present system can determine the necessary bend angles at these ½ cm increments. In accordance with one embodiment, the software does generate bend data for the minimum permissible increment, in this case ½ cm. However, it is expected that the making a bend every ½ cm is too cumbersome and time consuming, and generally not necessary to produce a well-contoured rod for implantation. In many cases, the surgeon will prefer a "simple" bend—i.e., one with the fewest number of bend points—versus a "smooth" bend—i.e., one that produces a smoothly contoured rod and that necessarily requires more bend points. In one feature of the invention, a GUI allows the surgeon to determine the bend type—simple or smooth—and in some embodiments to select a sliding scale between simplest and smoothest bend type.

In determining the "simplest" bend, the object is to eliminate as many bend points as possible without compromising the overall shape of the rod and the ability of the contoured rod to mate with the implanted bone screws. In a first step, the bend point with the smallest bend angle is eliminated. In alternative embodiments, other bend points are chosen first, either arbitrarily, to spread the bend points apart or to limit the number and size of bends at or near an attachment point and the like. Regardless, the remaining adjacent bend points are then connected with a straight line. However, not all small bend angle points can be eliminated. The present system thus discriminates in identifying-small bend angle points that cannot be eliminated where eliminating the particular point would:

1) pull the rod away from any of the screws by an amount exceeding the values ImplantTolerancesXY or ImplantTolerancesXZ. This determination is made using the ErrorXZ and ErrorXY equations above using the closest remaining bend points $(x_1, y_1, z_1)$ and $(x_2, y_2, z_2)$ on either side of the screw position $(x_{screw}, y_{screw}, z_{screw})$;

2) cause any of the bend angles to exceed the maximum desired bend angle. A bend angle is determined by the arc-cosine of the dot product of the vectors $V_{12}$ and $V_{23}$ formed between adjacent bend points $(x_1, y_1, z_1)$-$(x_2, y_2, z_2)$ and $(x_2, y_2, z_2)$-$(x_3, y_3, z_3)$.

3) cause the rod to screw interaction to exceed that allowed by the MaxHeadAngle value, calculated using the equation set forth above for calculating Rod2ScrewAngle.

It can be appreciated that for the "simplest" bend case, the maximum permitted bend angle may be larger than for the "smoothest" bend case. Conversely, the smoother bend case will necessarily include more intervening bend points along the length of the rod.

Figure 15A:
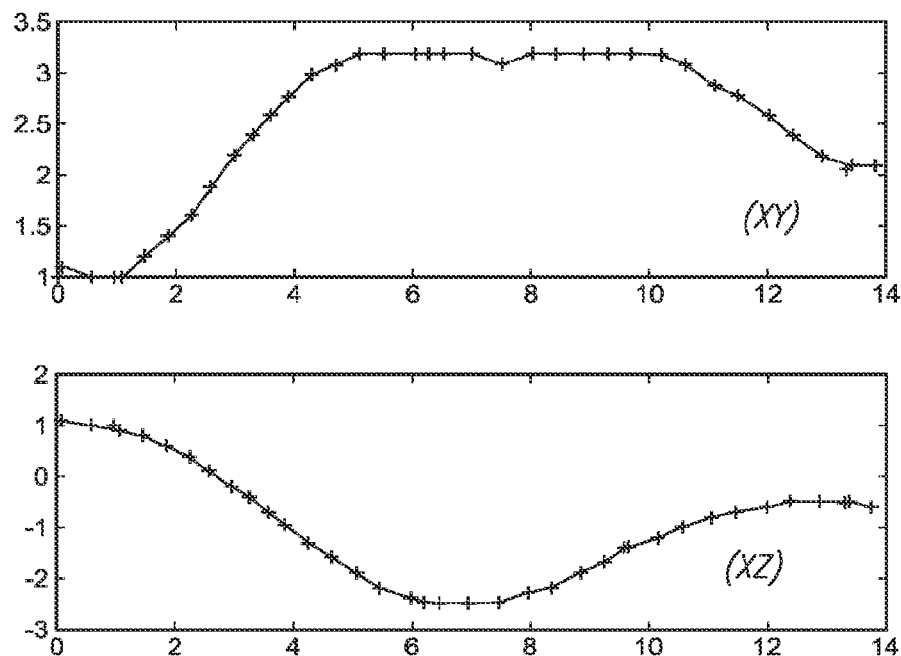
FIGS. 15a-k shows a sequence of bend curves in the XY and XZ planes with successive bend points eliminated to simplify the bend curve.
Figure 15B:
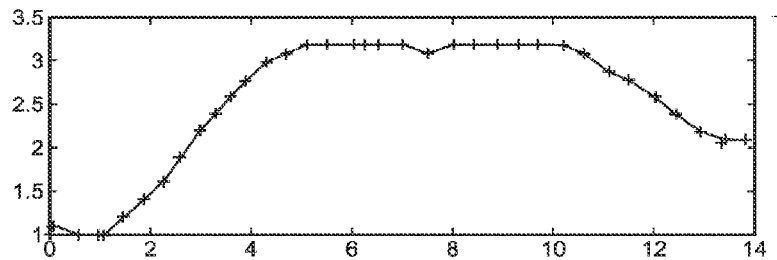
Figure 15B:
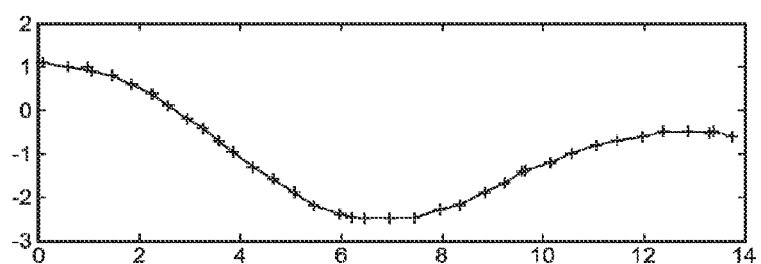
Figure 15C:
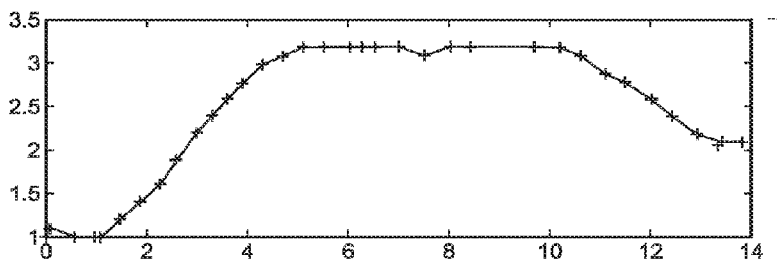
Figure 15C:
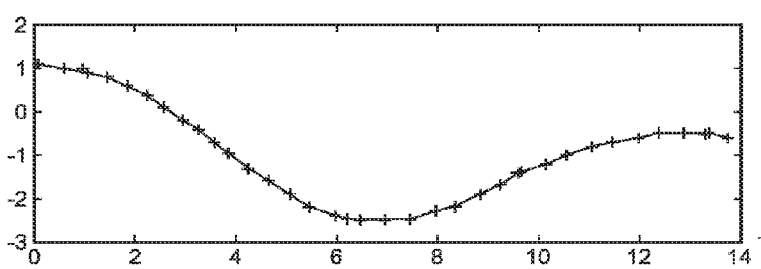
Figure 15D:
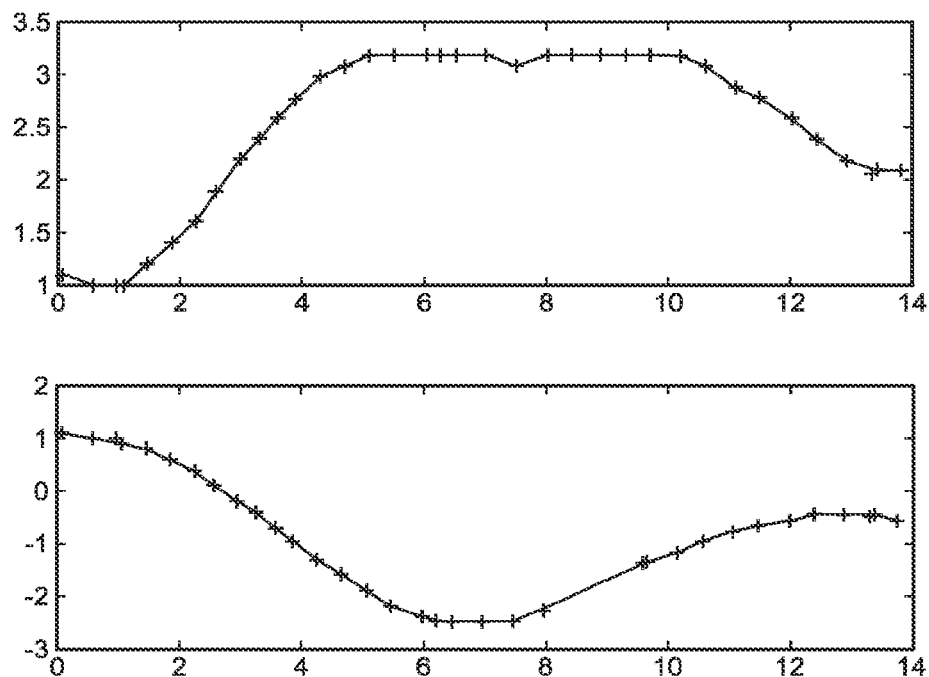
Figure 15E:
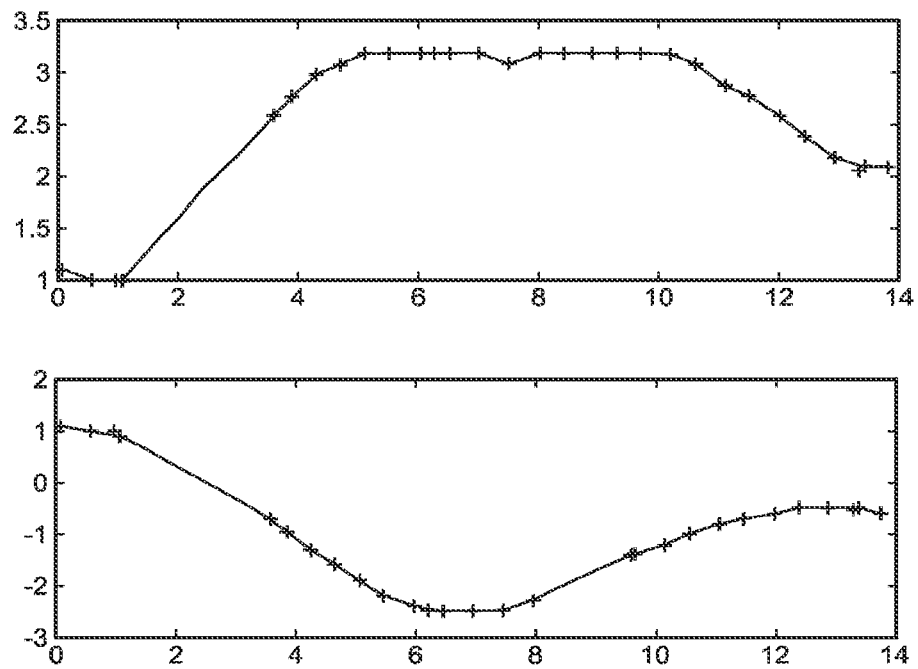
Figure 15F:
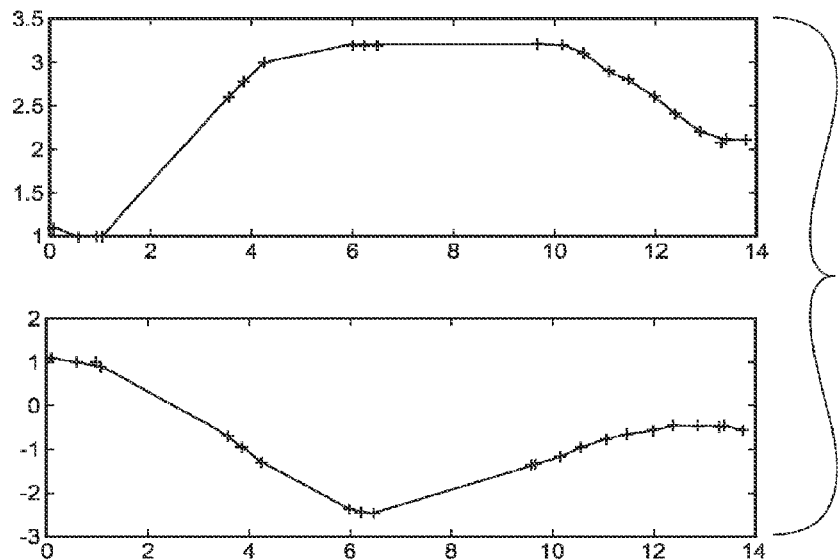
Figure 15G:
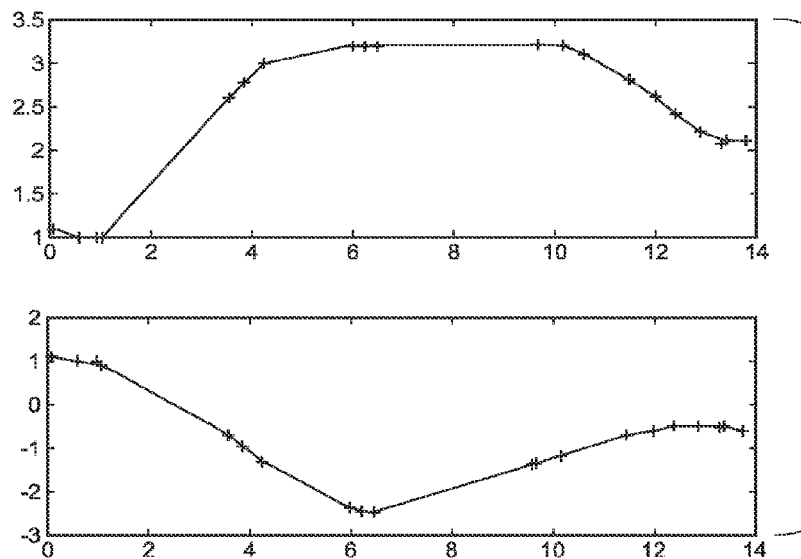
Figure 15H:
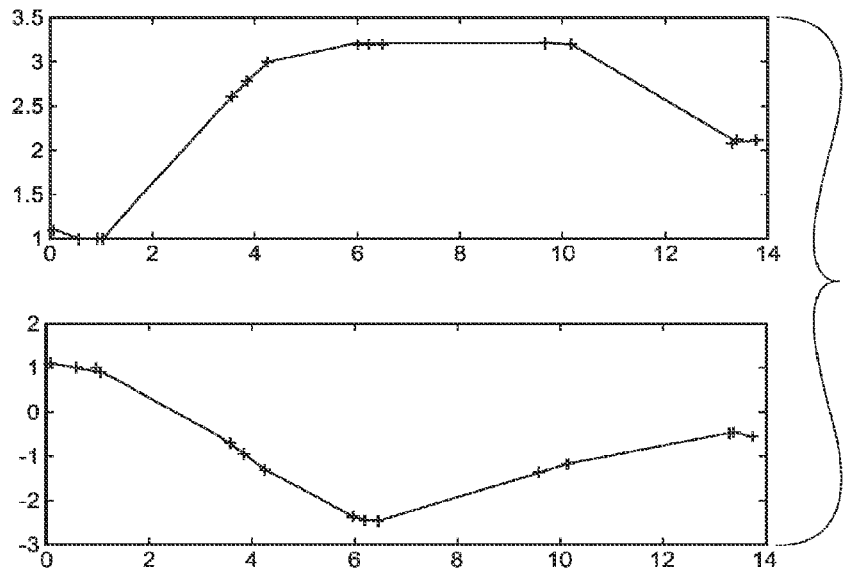
Figure 15I:
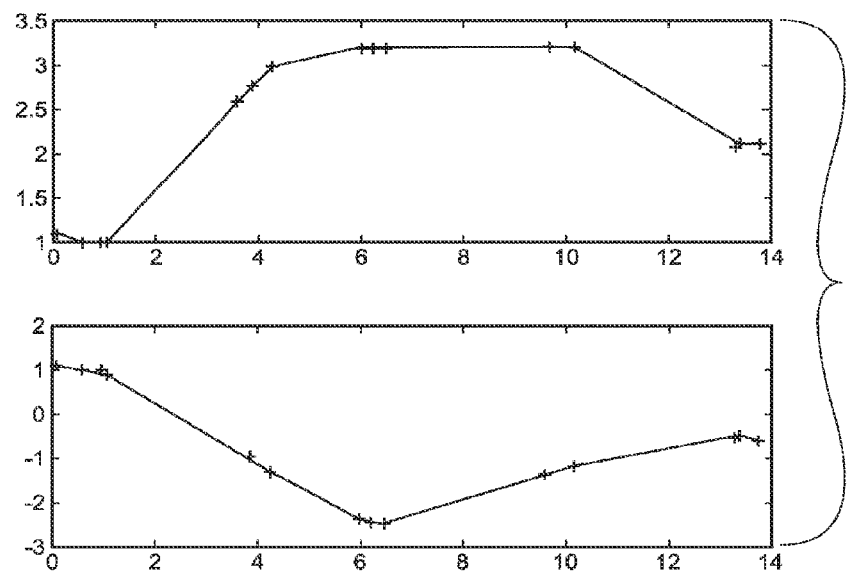
Figure 15J:
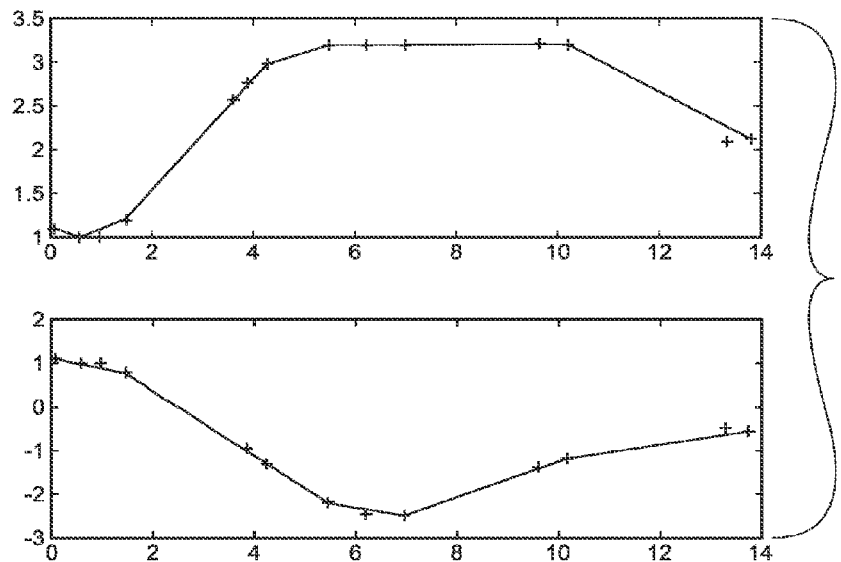
Figure 15K:
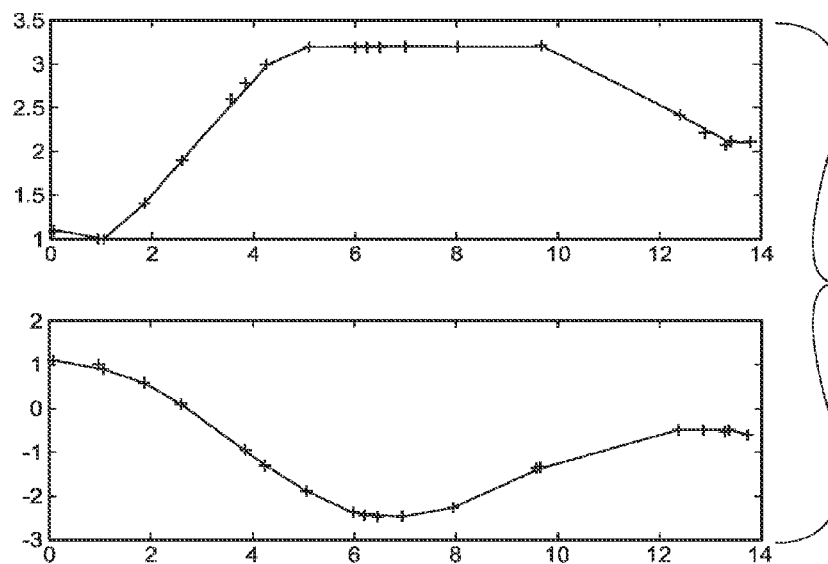

An exemplary bend reduction process is depicted in the sequence of FIGS. 15a-15j. The XZ and XY plane calculated rod contour is illustrated in FIG. 15a with bends every ½ cm. In FIG. 15b, one bend point at the 9.5 cm location has been eliminated. In FIG. 15c, the immediately adjacent bend point at location 9.0 mm has been eliminated. It can be easily appreciated that the elimination of these two bend points does not significantly alter the overall contour of the rod. In FIG. 15d, the bend at location 8.5 cm has also been eliminated, again with no significant impact on the overall contour.

As also shown in FIG. 15d, the bend at location 1.5 cm has been eliminated. In successive steps, bends at points 2.0, 2.5, 3.0 and 3.5 are eliminated and replaced with straight line segments, as reflected in FIG. 15e. As the process continues, additional bend points are eliminated and replaced by straight line segments between the remaining adjacent points. Thus, the present system is operable to produce modified rod bend contours shown in FIGS. 15f-15j. A comparison between the bend map shown in FIG. 15a and that shown in FIG. 15j reveals that the number of bends has been significantly reduced—from 32 bends to 7 bends. While every nuance of the calculated contour is not present in the final reduced configuration, the overall shape of the rod follows the calculated design and is certainly sufficiently close to the optimum design to easily mate with the implanted screws.

As explained above, the process of reducing the number of bends is based in part on the maximum desired bend angle. In the final version shown in FIG. 15j, the maximum bend angle was 38 degrees. For a smaller maximum bend angle, 22 degrees, the contour will require a greater number of bends (12).

It can also be appreciated that the present system generates the series of bend point modifications depicted in the sequence of FIGS. 15a-15j. If the surgeon selects the simplest bend, the system will output bend data corresponding to FIG. 15j. If the surgeon selects the smoothest bend type, the output data will correspond to the initial bend curve shown in FIG. 15a. However, the surgeon may make the bend type selection on a continuum incorporating aspects of both simple and smooth bends. More particularly, any one of the modified bend configurations in FIGS. 15b-15i may be selected as corresponding to a ratio of simple and smooth, as would a host of other bend point location options. Ultimately, the size of the maximum permissible bend angle chosen will cause the elimination of certain bend locations and not others, with greater number of bends associated with smaller permissible maximum bend angles and overall smoother resultant shaped outputs.

In accordance with one embodiment of the invention, a GUI is provided for the surgeon to input data and make selections to produce bend data. It is understood that the surgical objects to be achieved by the bent linking device or rod may determine the eventual nature of the bend data. Such surgical objectives include to address, straighten, or alter abnormalities in alignment of the body part(s) of the patient; create, lessen or eliminate deformities; reduce or impose changes in alignment; or the addition or elimination of stresses.

Figure 16:
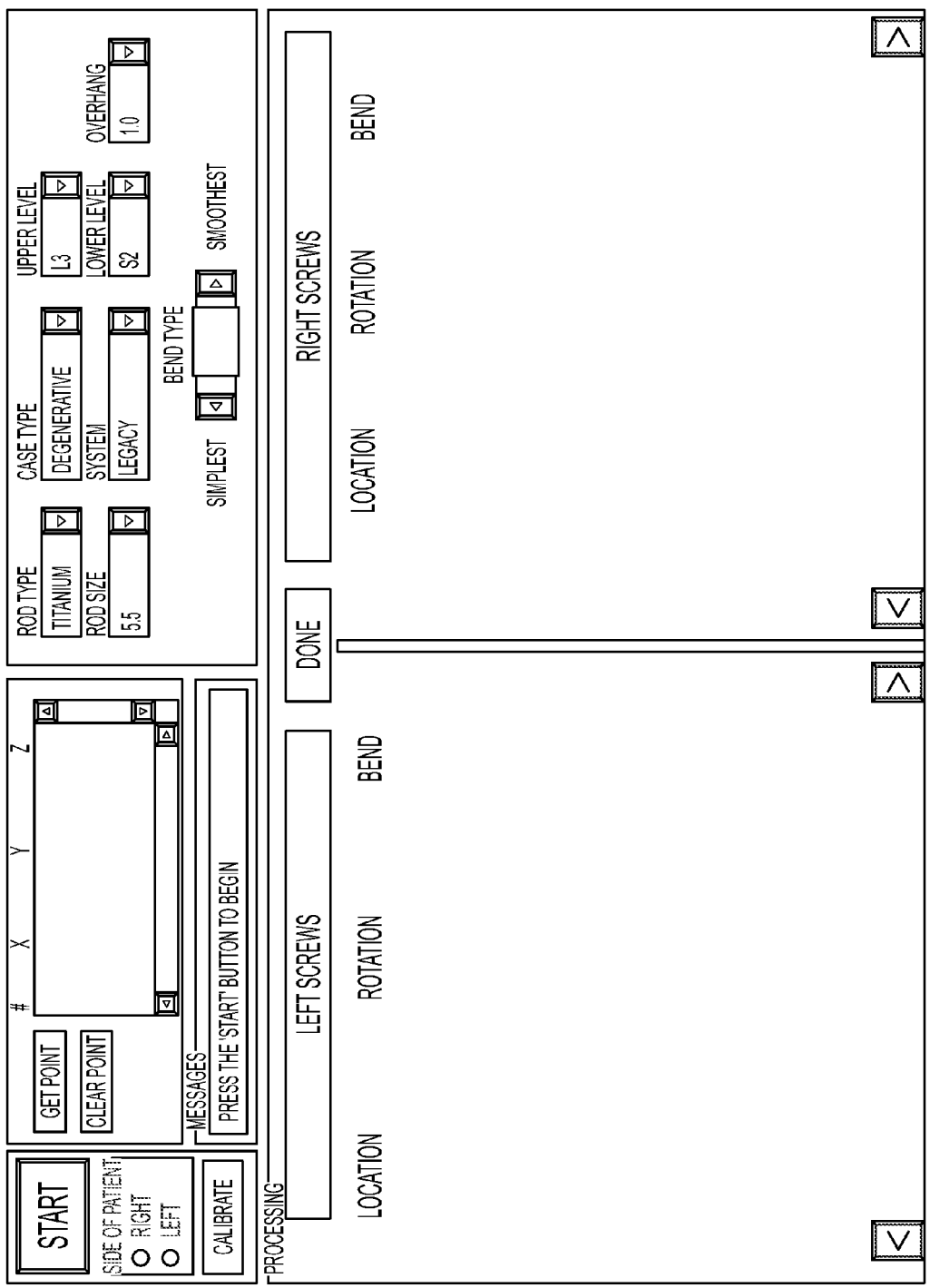
FIG. 16 is a representation of a graphical user interface (GUI) for permitting user input and displaying information to the user during the operation of the system of the present invention.

The GUI in one specific embodiment is illustrated in FIG. 16. The GUI may incorporate pull-down menus for entry of case-specific information such as rod type and size, case type, implant system, the range of instrumented levels and the amount of overhang of the rod beyond the upper and lower levels. The GUI may also include a sliding scale for selection of bent type, as discussed above. A message panel indicates the action to be taken on the GUI, such as "Press the 'Start' button to begin", identifying the orientation of the screw location data during digitizing and calculating the bend profile.

Figure 17:
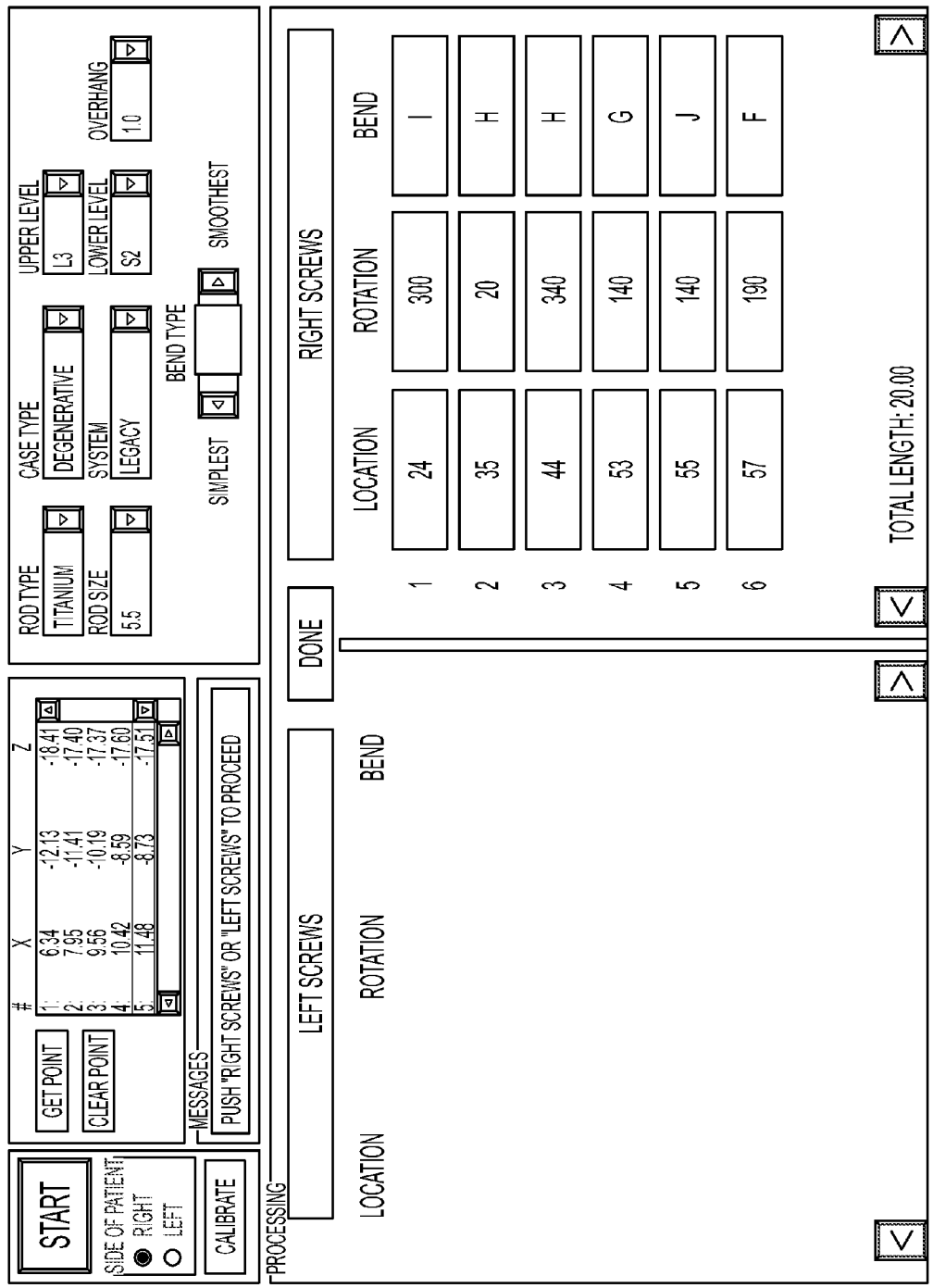
FIG. 17 shows the GUI of FIG. 16 after a bend curve has been calculated for a particular spinal construct.

The x, y, z location for the implanted screws is input through the GUI, resulting in the screw location data shown in the data box adjacent the "Get Point" button shown in FIG. 17. This screw location information may be obtained in a conventional manner, as described above, such as using known 3D digitizers. In some cases, it is difficult to obtain accurate data with the stylus provided with typical 3D digitizer systems. It is especially difficult to obtain accurate indications of the angle of the head of the fastener to which the rod or plate is to be engaged after contouring. Accordingly, one aspect of the present invention contemplates a digitizer probe that can be integrated with the digitizer instrument of these prior systems. In one embodiment, the digitizer probe 200, shown in FIG. 20, includes an elongated body 201 terminating in a top 202. The body preferably tapers along portion 206 to the tip 202. The proximal portion of the body is in the form of a shaft 204 that is configured at its proximal end 205 to mate with the digitizer instrument. Alternatively, the probe 200 can be formed as an integral part of the digitizer instrument.

The probe 200 is configured to mate with the head 192 of a fastener, such as the poly-axial fastener 190 shown in FIG. 20, or head 292 of the fastener 290 shown in FIG. 23. The fastener head includes a tool recess 194 that is configured to engage a driving tool. In a typical fastener, the recess is configured as a hex socket or a TORX socket. The tip 202 of the probe is configured to fit snugly within the recess 194. In one embodiment, shown in FIG. 21, the tip 202 is circular in cross-section with the radius of the tip slightly smaller than the flat dimension of the recess 194. In an alternative embodiment, the tip 202' may be complementary configured with the recess, as shown in FIG. 22. In this embodiment the tip 202' has a hex configuration to mate with the hex socket 194. The probe 200 with the tip 202' may be disengaged from the digitizer instrument once the fastener locations have been determined and engaged to a driving tool.

The tip 202 has a length sufficient to be fully seated within the recess 194 (or the recess 294 of the screw 290 shown in FIG. 23). This interface helps ensure that the probe 200 is aligned with the fastener 190 so that the angular orientation of the fastener can be accurately determined. In some cases the fastener includes a yoke 195 for a poly-axial connection to the fixation rod. The arms 196 of the yoke form a U-shape to receive the fixation rod. The arms 196 may also provide a guide for alignment of the probe 200, particularly by contact with the tapered portion 206. The tapered portion thus ensures that the probe is in stable engagement with the fastener 194 even when the tip 202 is not fully seated within the recess 194.

A probe 210 is shown in FIG. 24 that is configured to engage the poly-axial fastener 190. The probe 210 includes a body 211 defining a central hub 212 and outer wings 214. The body further includes a shaft 216 that is sized and configured to integrate with the digitizer instrument. The hub and wings are configured to be juxtaposed with the opposite faces of the arms 196 of the yoke 195. The central hub 212 can be configured as a generally rectangular body that extends along the U-shaped opening of the yoke. Alternatively, where the yoke 195 defines a cylindrical cavity between the arms 196, such as to engage a set screw, the central hub 212 may be circular in cross-section to mate with the cavity. Likewise, the wings 214 are configured complementary to the outer surface of the arms 196 of the yoke. In a typical case, the arms of the yoke have a cylindrical outer surface, so the interior surface of the wings 214 are similarly cylindrical. This configuration allows the probe 210 to be used as a tool to re-orient or rotate the yoke 195 relative to the fastener 190.

The distal end 213 of the central hub 212 may be configured to engage the upper surface of the head 192 of the bone screw. Alternatively, the hub and wings may define a perimeter channel 218 that is configured to contact the top of the arms 196 of the yoke 195. In either case, the distal end 213 or the channel 218 stabilize the probe 210 when it engages the fastener 190 to ensure an accurate angular orientation of the probe. It can be appreciated that in this embodiment, the probe 210 may be keyed off the position and orientation of the yoke 195, rather than the screw head 192. In this case, the distal end 213 of the central hub is sized to provide clearance from the upper surface of the head.

It is contemplated that the probes 200 and 210 can be provided in configurations for mating with specific fastener types. Moreover, the length of the probe from the tip 202 to the proximal end of the shaft 206 of the probe 200 (or from the distal end 213 or channel 218 to the end of the shaft 216 in the embodiment of FIG. 24) is precisely known. This length can be calibrated into the digitizing routine to yield accurate data about the fastener position in six degrees of freedom, including the angular orientation of the mating features of the fastener. It is further contemplated that the probe 200/210 itself may be used to identify the angular orientation of the attachment element relative to the spine. In this approach, the digitizing instrument can contact the probe at its proximal end and at a known position adjacent the interface of the probe with the attachment element. The three-dimensional positional data for these two points can then be used to calculate the spatial angle of the attachment element. This spatial angle can be used particularly to determine wither the yoke 195 of certain attachment elements are properly oriented to accept a linking element, such as a spinal rod.

The probes 200, 210 may be formed of any biocompatible material that is sufficiently rigid to resist bending during the digitization process. Where the probe incorporates a "tool" feature, such as the tip configuration shown in FIG. 22, the probe must be able to transmit sufficient torque to the fastener.

Returning to FIG. 16 et seq., the present invention contemplates that a surgeon may desire to achieve a predetermined deformity correction. However, the digitized data corresponds to the actual position of the mating elements of the fasteners. In certain cases, this data is desirable since the object is to mate a bent rod to engage the fasteners in those very positions. However, in some cases, a surgeon may find it desirable to impart a predetermined correction to the existing curvature of the spine. For instance, in the case of a scoliosis condition it may be desirable to shift certain vertebrae in the transverse direction to reduce the scoliotic curvature. The GUI of the present system allows the surgeon to modify the fastener position data form the original digitized positions. In the subsequent steps of the procedure, the bent configuration of the spinal rod is determined and the surgeon can evaluate the resultant predicted curvature or shape to determine whether the desired correction has been obtained. If necessary the surgeon can repeat the initial step of establishing the fastener location and adjust the amount of modification to achieve the desired resultant shape.

After all of the screw location data has been entered, the system calculates the bend data based upon the algorithms described above and the surgeon's selection of bend type. The output on the GUI is a sequence of bend data, as shown in FIG. 17. In the illustrated embodiment, the bend data is tailored to the bending tool 70 described herein. The magnitude of the bend in this embodiment is represented by letters, in this case "F" thru "I", that correspond to specific bend angles that are predefined on the bending tool 70. For example, an "I" bend is greater than an "H" bend, and so on.

Once the bend points are established, the present system translates the bend point data into the instructions for the bending tool. As indicated above, for the tool 70 described herein, only three data points are necessary—all derived from the distance from the last bend, the rotation of the rod compared to the bend angle of the last bend and the amount of the bend. These values can be obtained from the relationships described below.

The distance between bends is given by the expression $((x_2-x_1)^2+(y_2-y_1)^2+(z_2-z_1)^2)^{1/2}$. The location of the bends is a cumulative summation of the distances between bend points.

The rotation between bends can be determined by the angle between the normal to planes containing successive bend points. For instance, for the rotation between bend 2 and bend 3, a determination is made of the angle between the normal to the plane $N_{123}$ containing the three bend points $x_1y_1z_1$, $x_2y_2z_2$, and $x_3y_3z_3$ and the plane $N_{234}$ containing the three bend points $x_2y_2z_2$, $x_3y_3z_3$, and $x_4y_4z_4$. The rotation between these bends is then represented by the arc-cosine of the dot product of $N_{123}$ and $N_{234}$.

The amount of the bend is the angle between the vectors containing the bend points. Thus for the example with bend 2 and bend 3, the amount of the bend is given by the arc-cosine of the dot product of the vectors $V_{12}$ and $V_{23}$.

It is contemplated that the amount of the bend at each bend point may be altered to account for springback of the material. For a typical case the springback will be derived from a linear function, approximated as 14 degrees for a 5.5 mm stainless steel rod, or 13 degrees for a 5.5 mm titanium rod, based on the elasticity of the two materials.

Figure 18B:
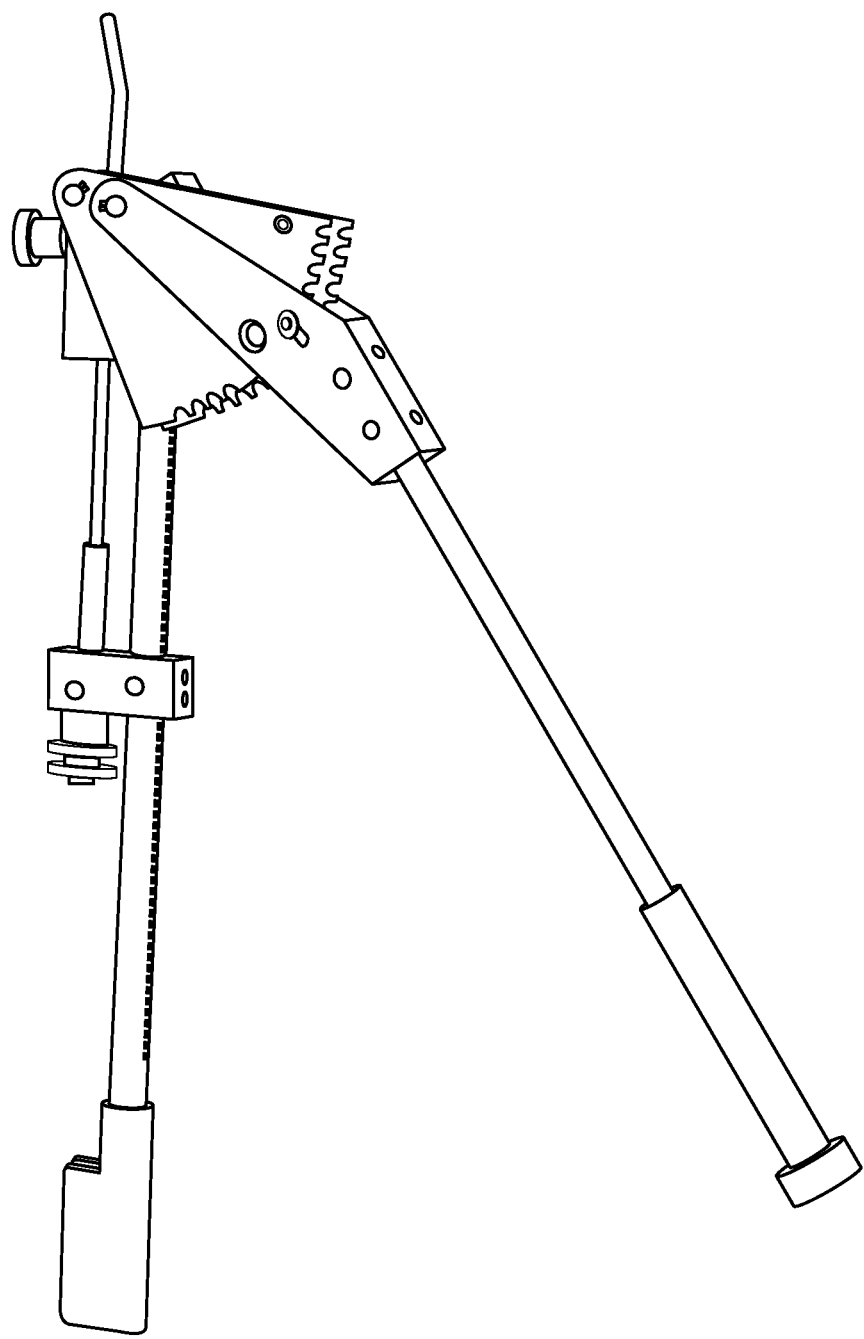

The manner in which the bend data is implemented using the bending tool 70 is depicted in FIGS. 18a-d. In FIG. 18a, the first bend is made using the tool. With the rod 10 held in place by the collet 75 (see FIG. 7), the slide block 76 is moved to the axial location "24" along the handle 72 identified in the bend data. In addition to the click stops 77 described above, the handle 72 may also incorporate numerical indicia 77a that corresponds to the axial position number in the bend data shown on the GUI.

The bend rotation value of "300" in the bend data is implemented by rotating the collet knob 90 to the appropriate indicia 90a. Rotating the collet knob rotates the rod 10 relative to the bending dies 81, 82, as described in more detail above. Finally, the bend magnitude or angle corresponding to the value "I" in the bend data, is set using the angle gauge 85. In addition to the ratchet teeth 86 used to establish the 5 degree angle increments, the angle gauge 85 may incorporate indicia 86a corresponding to the bend values "F"—"I" in the bend data of the present illustration. The gauge may include many more incremental bend angle indicia, ranging from "A" to "N" in the embodiment illustrated in FIG. 18a, thereby providing 14 discrete bend angles. In another embodiment, nondiscrete or continuous bend angles could be employed as could either smaller or larger steps between angle choices. Once the components of the bending tool have been set according to the calculated bend data, the bend is made, as shown in the figure.

Figure 18C:
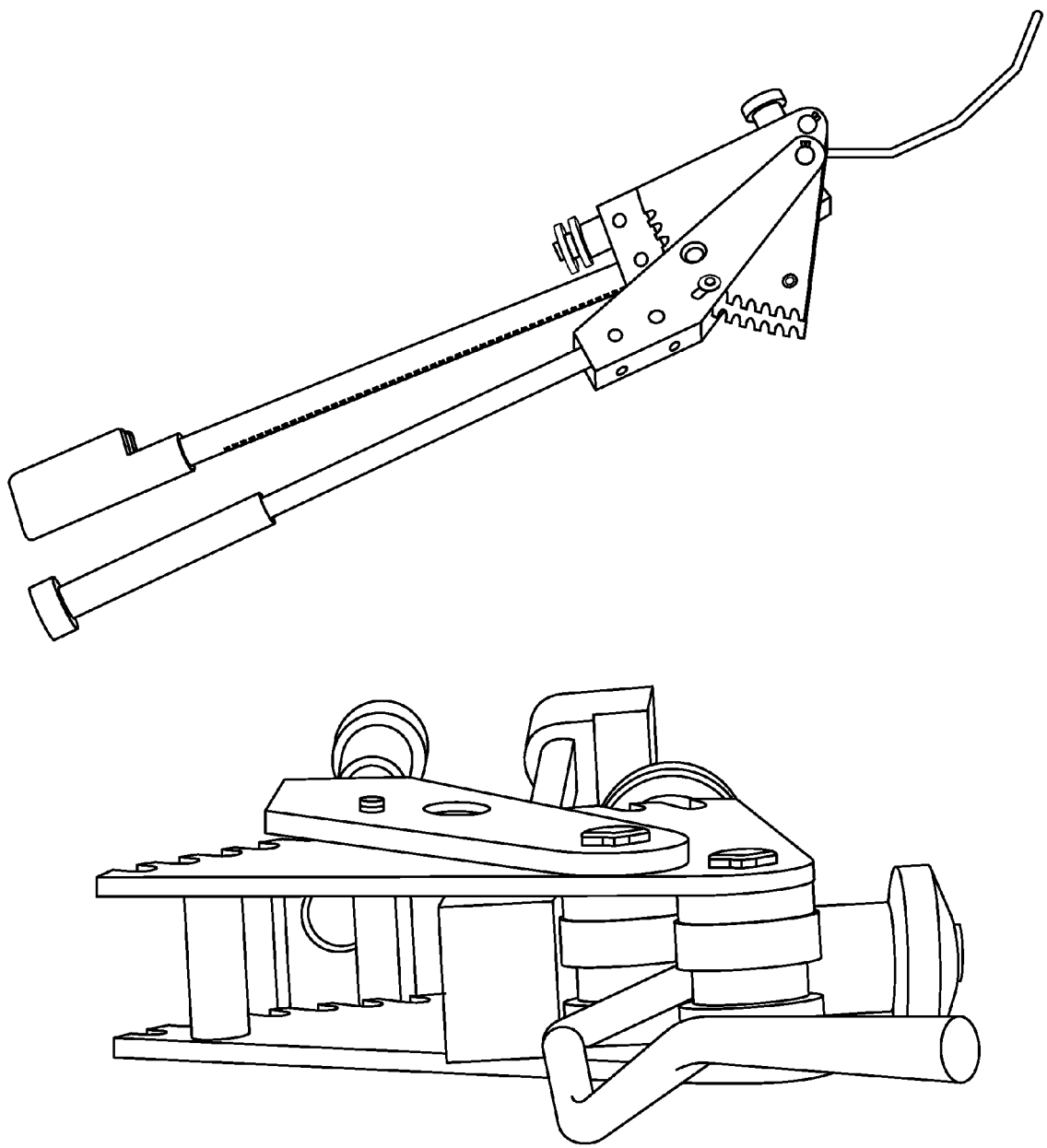
Figure 18C:
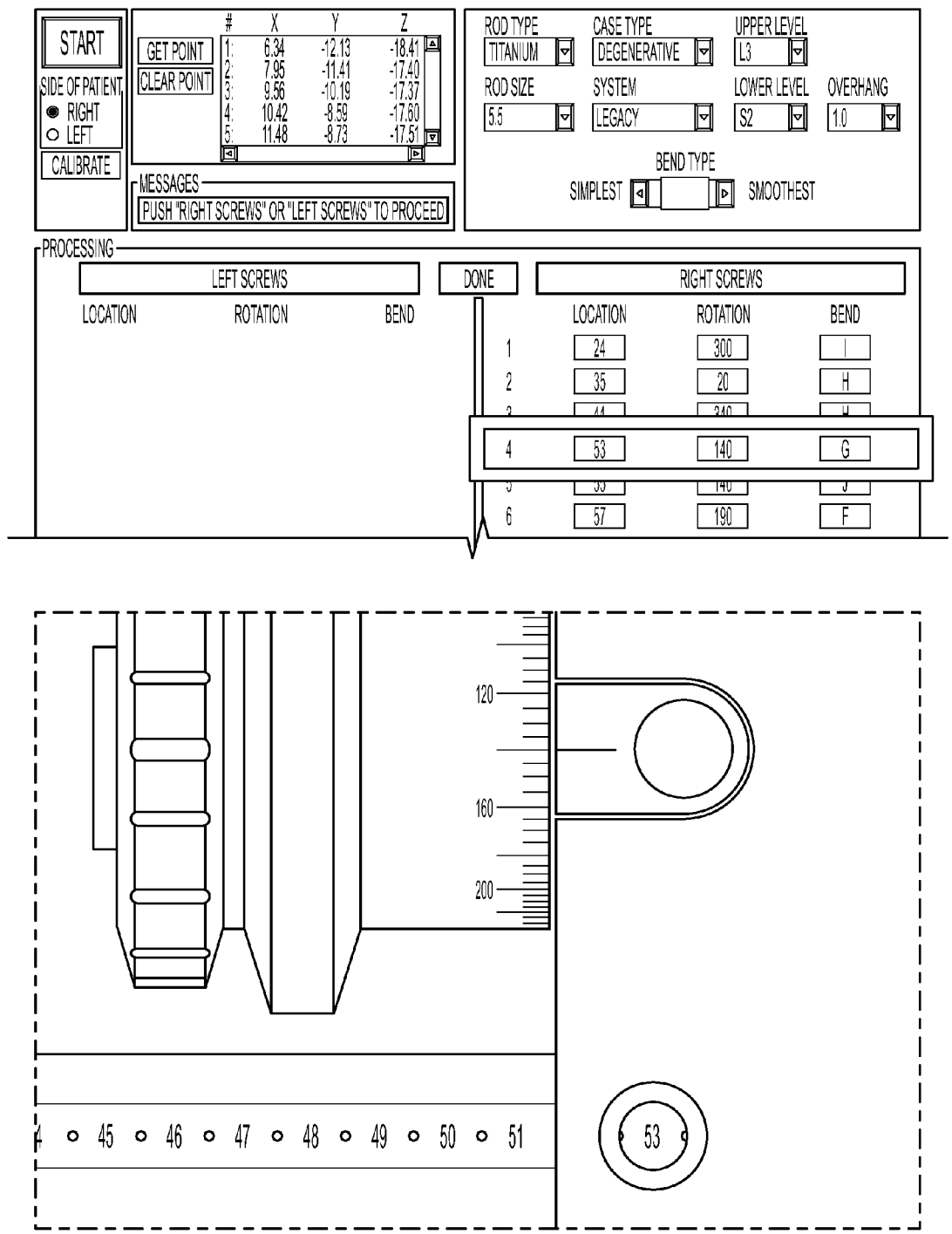
Figure 18D:
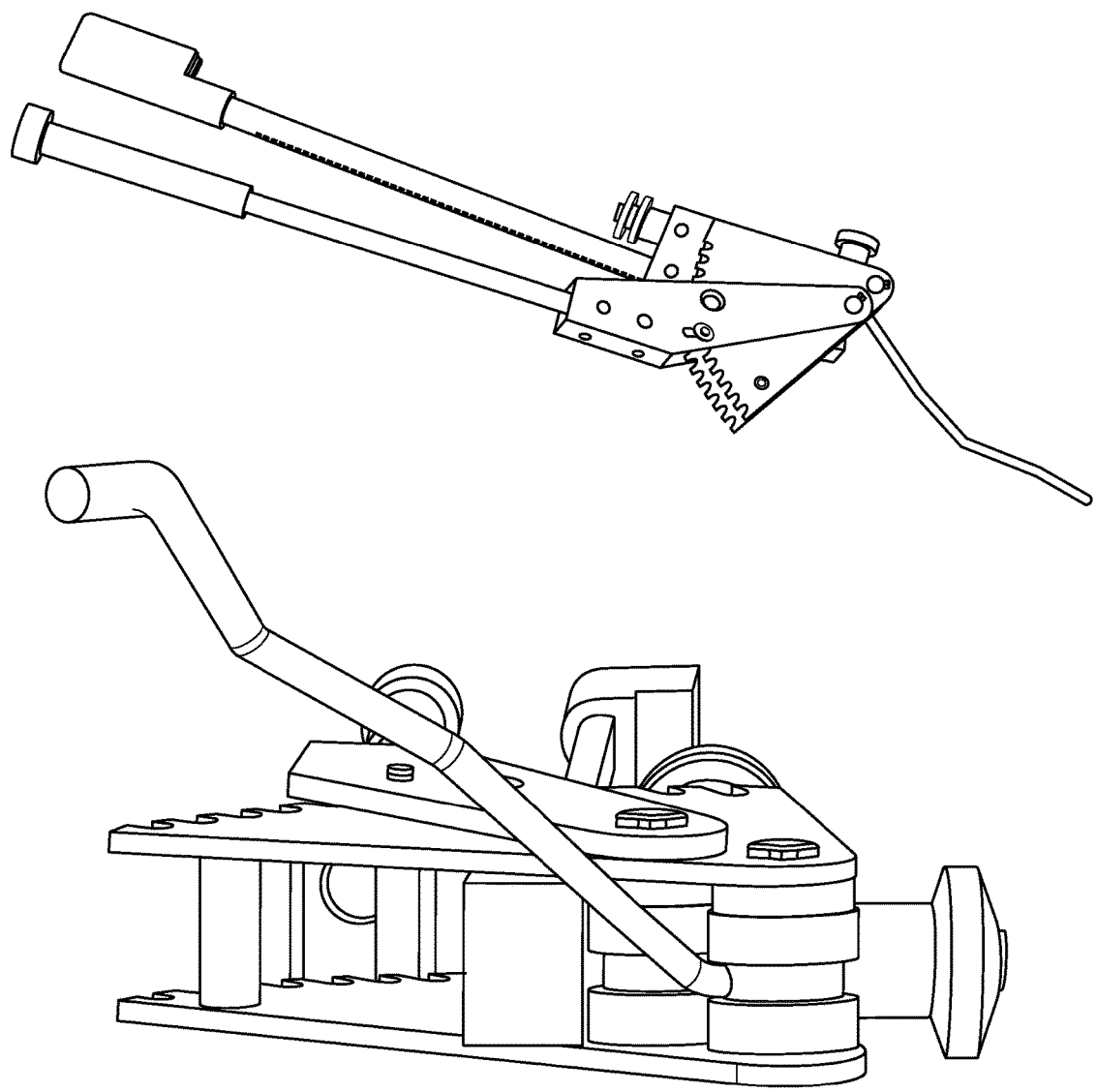
Figure 18D:
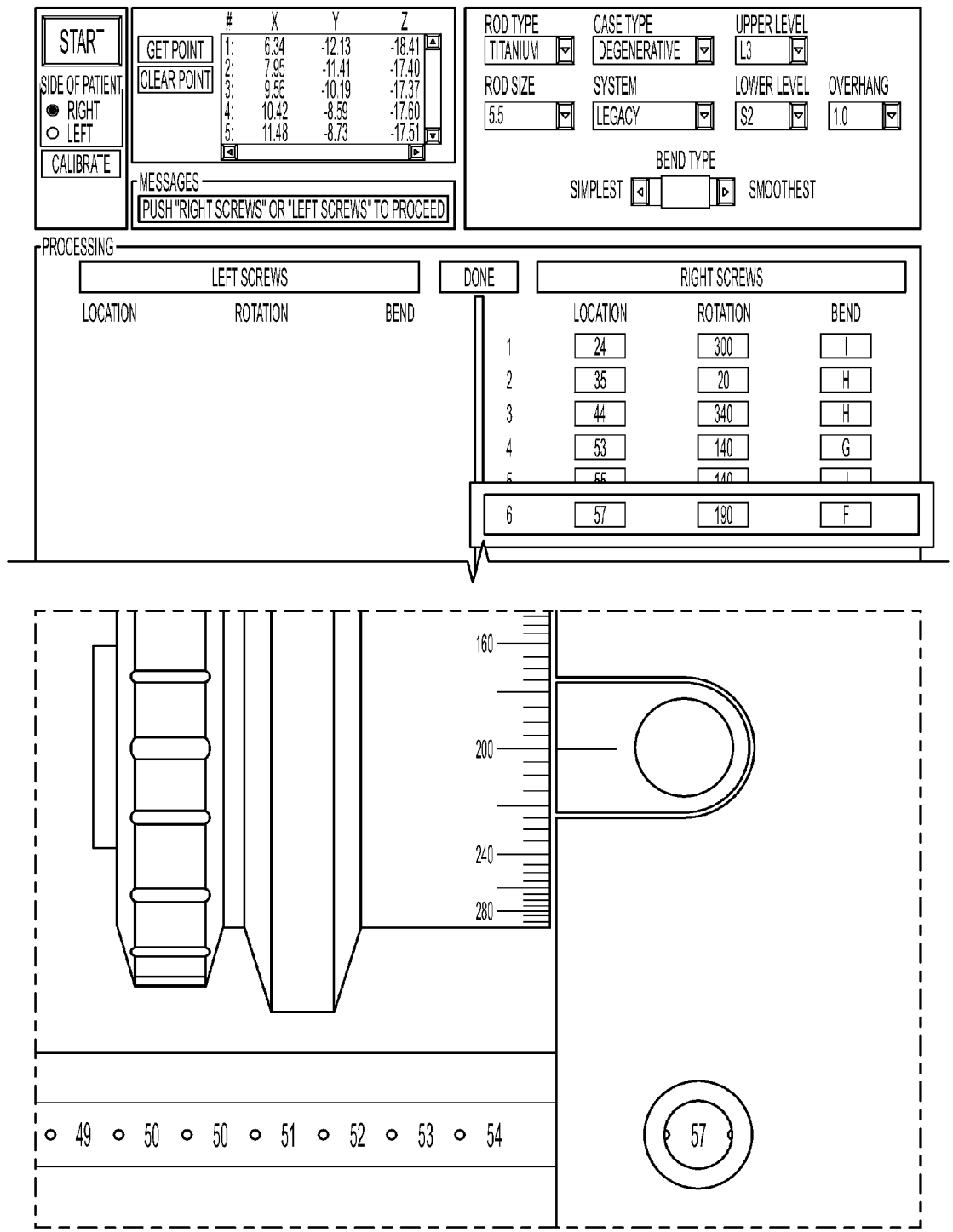
Figure 19:
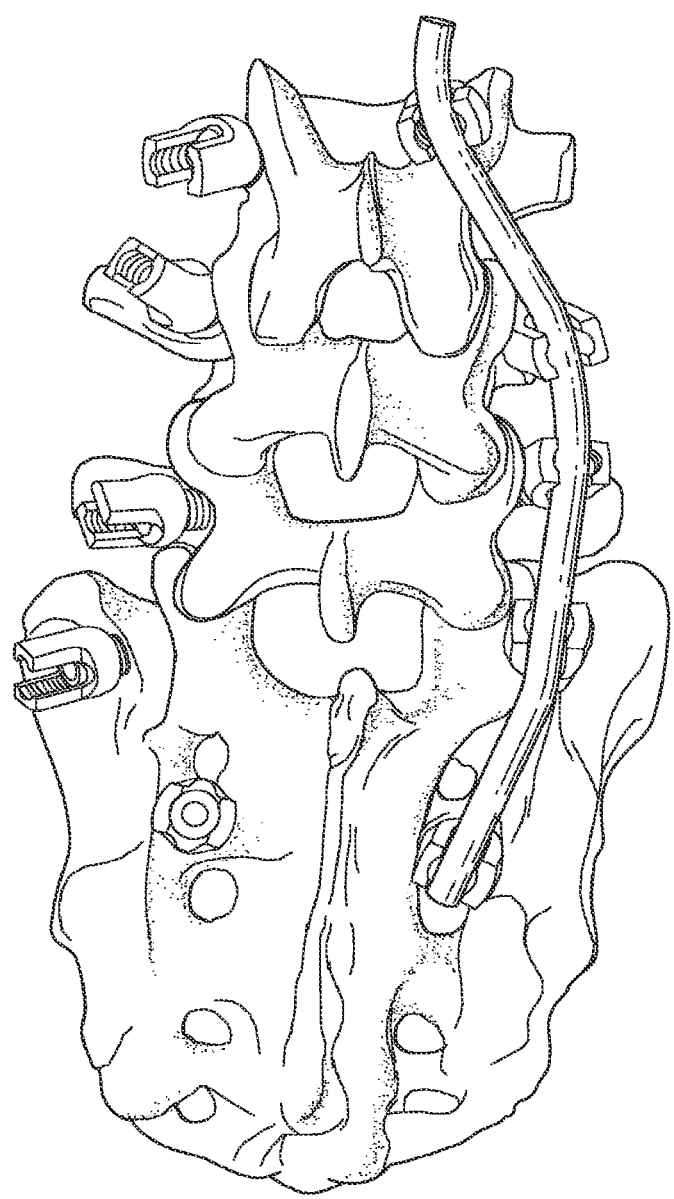
FIG. 19 shows a rod bent according to the bending instructions displayed on the GUI shown in FIG. 16.

The second bend is accomplished as shown in FIG. 18b. In this case, the slide block 76 is advanced to the axial location "35", the collet knob 90 is rotated to the 20 degree position, and the bend angle "H" is selected on the angle gauge 85. The second bend is then made. The effect of the third and fourth bends are shown in FIG. 18c, with the understanding that the bending tool 70 is manipulated according to the bend data, as described above. The final bend is made as shown in FIG. 18d, resulting in a rod 10 that is bent to follow a three-dimensional contour calculated to mate with an array of screws implanted in a patient's spine, as shown in FIG. 19.

In some procedures the spine is instrumented with multiple linking devices. For instance, attachment elements and linking elongated rods may be positioned on either side of the spinous processes. The two rods are typically interconnected using transverse connectors to provide a rigid "scaffold" for supporting the spine. The method described above can be used to generate appropriately shaped rods to be positioned on either side of the spinal midline. The bend curves calculated for each rod may be used to determine the size of any transverse connectors or linking devices that may be utilized.

The above examples and particular embodiment are not intended to limit the claims which follow. A variety of changes to the gauges, levers and the device and method of determining the shaping parameters is within the scope of the present invention.

What is claimed is:

1. A method for shaping a surgical linking device comprising:
   (a) generating a bend curve having a plurality of bend points along the length of the surgical linking device, wherein the bend curve is based on data for a location of at least one attachment element; and
   (b) generating bending instructions for bends to be performed on the linking device by a bending tool at each of the bend points.

2. The method of claim 1, further comprising developing a curve function to approximate a desired location of the at least one attachment element.

3. The method of claim 2, further comprising calculating a location of the linking device shaped according to the curve function at the desired location of the at least one attachment element.

4. The method of claim 3, further comprising calculating an error based on the difference in the calculated location of the linking device and the desired location of the at least one attachment element and determining if such error exceeds a tolerance range.

5. The method of claim 4, wherein bend points are eliminated if the determined error exceeds the tolerance range.

6. The method of claim 4, wherein the step of calculating an error includes applying a least mean squares approach over all of the desired attachment element locations.

7. The method of claim 1, comprising a plurality of bend curves, wherein at least two bend curves are in each of two non-coplanar planes.

8. The method of claim 7, wherein the two planes are orthogonal.

9. A method for shaping a surgical linking device comprising:
   (a) providing digitized data for a location of at least one attachment element;
   (b) developing a curve function to approximate a desired location of the at least one attachment element;
   (d) calculating a location of the linking device shaped according to the curve function at the desired location of the at least one attachment element;
   (e) generating a bend curve having at least one bend point along the length of the linking device using the curve function, wherein the bend curve is based on the digitized data for the location of the at least one attachment element; and
   (f) generating bending instructions for at least one bend to be performed on the linking device by a bending tool at the at least one bend point.

10. The method of claim 9, further comprising calculating an error based on the difference in the calculated location of the linking device and the desired location of the at least one attachment element and determining if such error exceeds a tolerance range.

11. The method of claim 10, wherein the at least one bend point is eliminated if the determined error exceeds the tolerance range.

12. The method of claim 10, in which the linking device is a rod and a head portion of the attachment element includes a channel for receiving the rod, wherein the step of determining a tolerance range is based on the maximum angle through which head portion may pivot relative to the bony structure.

13. The method of claim 9, wherein digitized data is provided for anatomical points between a plurality of attachment elements that must be avoided by the linking device when it is engaged to the attachment elements.

14. The method of claim 9, further comprising applying a smoothing function to the curve function.

15. A method for shaping a surgical linking device comprising:
   (a) generating a bend curve having at least one bend point along the length of the linking device, wherein the bend curve is based on a desired location of at least one attachment element; and
   (b) generating bending instructions for bends to be performed on the linking device by a bending tool at each of the at least one bend point.

16. The method of claim 15, wherein the bend curve is based at least in part on digitized data of the location of the at least one attachment element.

17. The method of claim 15, further comprising developing a curve function to approximate the desired location of the at least one attachment element.

18. The method of claim 17, further comprising calculating the location of the linking device shaped according to the curve function at the desired location of the at least one attachment element.

19. The method of claim 18, further comprising calculating an error based on the difference in the calculated location of the linking device and the desired location of the at least one attachment element and determining if such error exceeds a tolerance range.

20. The method of claim 17, further comprising applying a smoothing function to the curve function.

* * * * *